(12) United States Patent
Schultz et al.

(10) Patent No.: US 8,309,370 B2
(45) Date of Patent: Nov. 13, 2012

(54) PLASMON RESONANT PARTICLES, METHODS AND APPARATUS

(75) Inventors: Sheldon Schultz, La Jolla, CA (US);
David A. Schultz, La Jolla, CA (US);
David R. Smith, La Jolla, CA (US);
Jack J. Mock, Del Mar, CA (US);
Thomas J. Silva, Golden, CO (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 13/157,151

(22) Filed: Jun. 9, 2011

(65) Prior Publication Data
US 2011/0244479 A1    Oct. 6, 2011

Related U.S. Application Data

(60) Continuation of application No. 12/398,180, filed on Mar. 5, 2009, now Pat. No. 7,981,695, which is a continuation of application No. 09/740,615, filed on Dec. 18, 2000, now Pat. No. 7,501,288, which is a division of application No. 09/027,048, filed on Feb. 20, 1998, now Pat. No. 6,180,415.

(60) Provisional application No. 60/038,677, filed on Feb. 20, 1997.

(51) Int. Cl.
*G01N 33/553* (2006.01)

(52) U.S. Cl. .................................................... 436/525

(58) Field of Classification Search ................. None
See application file for complete search history.

(56) References Cited

U.S. PATENT DOCUMENTS

| | | | |
|---|---|---|---|
| 3,856,398 A | 12/1974 | Taylor | |
| 4,099,854 A | 7/1978 | Decker et al. | |
| 4,313,734 A | 2/1982 | Leuvering | |
| 4,416,998 A | 11/1983 | Adams et al. | |
| 4,481,091 A | 11/1984 | Brus et al. | |
| 4,877,647 A | 10/1989 | Klabunde | |
| 4,979,821 A | 12/1990 | Schutt et al. | |
| 5,023,139 A * | 6/1991 | Birnboim et al. | 428/402 |
| 5,025,147 A | 6/1991 | Durig et al. | |
| 5,075,796 A | 12/1991 | Schildkraut et al. | |
| 5,249,077 A | 9/1993 | Laronga et al. | |
| 5,322,798 A | 6/1994 | Sadowski | |
| 5,338,353 A | 8/1994 | Uchino et al. | |
| 5,376,556 A * | 12/1994 | Tarcha et al. | 436/525 |
| 5,449,918 A * | 9/1995 | Krull et al. | 250/458.1 |
| 5,451,525 A | 9/1995 | Shenkin et al. | |
| 5,479,024 A | 12/1995 | Hillner et al. | |
| 5,485,277 A | 1/1996 | Foster | |
| 5,501,949 A | 3/1996 | Marshall | |
| 5,552,086 A | 9/1996 | Siiman et al. | |
| 5,567,628 A | 10/1996 | Tarcha et al. | |
| 5,599,668 A | 2/1997 | Stimpson et al. | |
| 5,633,724 A | 5/1997 | King et al. | |
| 5,717,518 A | 2/1998 | Shafer et al. | |
| 5,792,667 A * | 8/1998 | Florin et al. | 436/147 |
| 5,815,278 A | 9/1998 | Johnston et al. | |
| 5,817,462 A | 10/1998 | Garini et al. | |
| 5,981,167 A | 11/1999 | Taremi et al. | |
| 6,025,202 A * | 2/2000 | Natan | 436/104 |
| 6,174,677 B1 * | 1/2001 | Vo-Dinh | 435/6.11 |
| 6,180,415 B1 | 1/2001 | Schultz et al. | |
| 6,344,272 B1 * | 2/2002 | Oldenburg et al. | 428/403 |
| 6,992,770 B2 | 1/2006 | Naya | |
| 7,869,030 B2 | 1/2011 | Zhong et al. | |
| 7,981,695 B2 * | 7/2011 | Schultz et al. | 436/525 |
| 2008/0268288 A1 * | 10/2008 | Jin | 428/800 |
| 2011/0014125 A1 | 1/2011 | Bossmann et al. | |
| 2011/0143953 A1 * | 6/2011 | Johnston et al. | 506/9 |
| 2012/0021967 A1 * | 1/2012 | Johnston et al. | 514/1.1 |
| 2012/0065123 A1 * | 3/2012 | Johnston et al. | 514/1.1 |

FOREIGN PATENT DOCUMENTS

WO    WO 97/40181    10/1997

* cited by examiner

*Primary Examiner* — Ann Lam
(74) *Attorney, Agent, or Firm* — Eleanor M. Musick; Procopio, Cory, Hargreaves & Savitch LLP

(57) ABSTRACT

A method and apparatus for interrogating a target having a plurality of plasmon resonant particles (PREs) distributed in the target are disclosed. In the method, a field containing the target is illuminated, and one or more spectral emission characteristics of the light-scattering particles in the field are detected. From this data, an image of positions and spectral characteristic values in the field is constructed, allowing PREs with a selected spectral signature to be discriminated from other light-scattering entities, to provide information about the field. Also disclosed are a novel PRE composition for use in practicing the method, and a variety of diagnostic applications of the method.

11 Claims, 10 Drawing Sheets scattered light
to objective lens

PLASMON RESONANT PARTICLES, METHODS AND APPARATUS

This application is a continuation of U.S. patent application Ser. No. 12/398,180 filed Mar. 5, 2009, which is a continuation of U.S. patent application Ser. No. 09/740,615 filed Dec. 18, 2000, issued as U.S. Pat. No. 7,501,288 on Mar. 10, 2009, which is a divisional of U.S. patent application Ser. No. 09/027,048 filed Feb. 2, 1998, issued as U.S. Pat. No. 6,180,415 on Jan. 30, 2011, which claims priority under 35 U.S.C. §120 to Provisional Application Ser. No. 60/038,677, filed Feb. 20, 1997, entitled "Preparation and Use of Plasmon Resonant Particles". All applications are hereby incorporated by reference in their entirety.

GOVERNMENT RIGHTS

This invention was made with government support under Grants No. DMR89-15815, DMR93-02913, BIR94-15294 and DMR96-23949, all awarded by the National Science Foundation. The government has certain rights in the invention.

FIELD OF THE INVENTION

The present invention relates plasmon resonant entities (PREs), or particles, to methods of interrogating a field containing PREs, and to apparatus for carrying out the method, and to various applications of PREs.

BACKGROUND OF THE INVENTION

There are a number of important commercial and scientific applications of interrogating a target for information about the target. For example, the aim of analyte diagnostic tests and methods is to detect the presence and/or amount of an analyte (the target). The target analyte may be detected by reacting the analyte with a detectable reporter that (i) can bind specifically to the analyte and (ii) is detectable with suitable detecting tools. The reporter may, for example, be a colored or fluorescence molecule, or a colloidal metal, or a reporter such as a radiolabel that requires special film or scintillation equipment for its detection.

In some diagnostic applications, it is desirable to detect proximity relationships in a target analyte, as evidenced by the interaction between two proximately located probes on the target analyte. This forms the basis of so-called homogeneous assays, where the presence of an analyte is determined by a detectable probe proximity effect observed when two distinct probes are brought together on closely spaced sites on the analyte. As an example, two fluorescent molecules, when brought together, may exhibit a detectable fluorescence quenching or a non-radiative energy transfer effect that acts to shift the Stokes radius between the excitation and emission peaks.

A chemical, biochemical, or biological target may be interrogated by a variety of chemical and spectrographic methods to determine chemical structure, the presence of certain chemical groups, or the environment of the chemical groups. Notable among these methods are magnetic resonance methods for determining chemical structure and chemical group environment, spectroscopic methods, such as UV, IR, Raman, ORD, and CD spectroscopy, for detecting specific chemical groups, and mass spectroscopy for determining structure by fragment molecular weight analysis.

Surface chemical analysis of a target sample may be carried out by bombarding the surface with high-energy particles, e.g., electrons, and detecting the energy of atoms that are ejected from the surface. Electron Spectroscopy for Chemical Analysis (ESCA) is an example of such an approach.

Often it is desirable to establish spatial and/or distance relationships in a target, generally requiring interrogation by microscopy. Light microscopy has the advantage of simplicity, ease of sample preparation, and the feature that the sample can be examined in a "wet" condition. Its disadvantage is the relatively low resolving power, directly related to the wavelength of the illumination source (in the 400-650 nm range) and inversely proportional to the numerical aperture of the lens systems (at best, about 1.4), limiting resolution to several hundred nm).

High-energy beam microscopes, such as the transmission electron microscope (TEM) and the scanning electron microscope (SEM) can achieve resolution down to the low nm range, but require a high-vacuum environment of the target sample, limiting applications with biological samples. Atomic force microscopy (AFM) is useful for interrogating surface features of a target sample, also with a resolution in the low nm range. The method is limited to surface effects.

Radiographic and scintigraphic methods for detecting and/or localizing sites of high-energy emission are also widely used. These methods tend to be quite sensitive, being able to detect very low numbers of high-energy emission events, but suffer from relatively high-cost and poor resolution when target spatial information is desired.

Despite the variety of methods currently available, there are a number of target-interrogation tasks of commercial and scientific interest that are difficult or impossible with current methods. Among these are:

1. Detecting single (or only a few) molecular events, such as the presence of one or a few binding sites, or one or a few enzymic sites on a target. This capability would open up new diagnostic applications, e.g., related to the presence or absence of specific intracellular events, and reduce the amount of sample material needed for a reliable assay and allow miniaturization of the assay.

2. Resolving sub-wavelength distance relationships in a biological target in a natural hydrated state. As noted above, subwavelength resolution by high-energy beam microscopy requires the sample target to be in a desiccated state, precluding the observation of natural cellular processes, including subwavelength movement of cellular components, and allows the user to perturb the sample during observation.

3. Direct spatial mapping of selected target sites on a biological target, such as direct mapping of selected sequences in a chromosome for purposes of chromosome mapping. Currently, this type of information is either not practical, or in the case of chromosome mapping, is not possible at high resolution and precise localization of gene sequences.

4. Optical reading of microencoded information. The ability to detect unique patterns of individual reporter groups would have important applications in forensics, information storage, metrology, and security identification microcodes.

It would therefore be desirable to provide a method and apparatus for interrogating a field for the type of information outlined above that is impractical or impossible to obtain by prior art methods.

It would also be desirable to apply the method to various diagnostics applications, to achieve improved sensitivity, spatial and distance information, ease of sample preparation, and flexibility in the type of target sample that can be interrogated.

SUMMARY OF THE INVENTION

In one aspect, the invention includes a method of interrogating a field having a plurality of PREs distributed therein.

The method includes the steps of illuminating the field with an optical light source, and detecting a spectral emission characteristic for individual PREs and other light scattering entities in the field. From this information is constructed a computer image of the positions and values of the emission spectral characteristic of individual PREs and other light-scattering entities present in the field, as a basis for discriminating PREs with a selected spectral signature from other light-scattering entities in the field, to provide information about the field.

The illuminating step may be carried out at different frequency bands, where the spectral emission characteristic of individual PREs and other light scattering entities in the field are detected at each such band.

Alternatively, the illuminating step may include exposing the field to a plurality of narrowband pulses of light which vary in duration, to detect variations in emitted light intensity produced by variations in duration.

In another embodiment, where the field preferably includes at least some non-spherical PREs, the illuminating step may involve exposing the field to polarized light at different orientations and/or different angles of incidence. The detecting step includes detecting a change in value of a spectral emission characteristic as a function of incident light polarization orientation or angle of incidence.

The detecting step may include simultaneously detecting the values of a spectral emission characteristic of individual PREs and other light scattering entities in the field at a plurality of defined spectral bands. Alternatively, the spectral emission characteristic values of individual PREs and other light scattering entities in the field may be detected sequentially at a plurality of defined spectral bands.

The PREs may be formed in or added to the field by metal enhancing nucleation centers in the field, by adding preformed PREs to a target in the field, or by making PREs at target sites in the field, e.g., by photolithographic methods.

The method may be practiced to discriminate PREs with a selected spectral signature from all other light-scattering entities in the field. The spectral emission characteristic that is detected, as a basis for the discrimination, is typically peak position, peak intensity, or peak width at half intensity of the spectral emission curve, peak halfwidth in the image plane, and/or polarization or angle of incidence response. Other emission spectral characteristics, such as response to pulsed beam illumination, are also contemplated.

The same spectral characteristics, either alone or in combination, are useful for discriminating (i) PREs from non-PRE light-scattering entities, (ii) one selected type of PRE from another, and (iii) PREs that are interacting through proximity effects from non-interacting PREs (typically PRPs).

In another embodiment, the PREs have a surface localized fluorescent or Raman-active molecular entities, e.g., Raman-active molecules, and the detecting includes detecting plasmon-resonance induced fluorescence emission or Raman spectroscopy emission from one or more of said entities.

The method may be carried out to yield information about (i) the total number of PREs of a selected type in a field, (ii) the spatial pattern of PREs having a selected range of values of a selected spectral characteristic in the field, (iii) a distance measurement between two adjacent PREs, particularly PREs separated by a distance less than the Rayleigh distance, (iv) a change in the environment of the field, e.g., dielectric constant, that affects the value of a plasmon resonance characteristics, or (v) motion of PREs in the field.

In another aspect, the invention includes apparatus for interrogating a field having a plurality of PREs distributed therein, for example, in practicing the above method for interrogating a field. The apparatus includes an optical light source for illuminating the field, and an optical detector for detecting values of a spectral emission characteristic of individual PREs and other light scattering entities in the field, when the field is illuminated by the light source.

Also included in the apparatus is an image processor operatively connected to the detector for constructing, from signals received from the detector, a computer image of the positions and detected values of the emission spectral characteristic of individual PREs and such other light-scattering entities present in the field, and a discriminator for discriminating PREs with a selected spectral signature from other light-scattering entities in the computer image, i.e., a selected range of values of a selected spectral emission characteristic. The apparatus is constructed to display (or store) information about the field based on the information about the selected PREs.

One preferred light source is a bright field/dark field lens for directing light onto the field. The illumination source may alternatively be a bright field lens, a dark field lens, a polarizer for producing polarized-light illumination source, such as a plane-polarized light source, a TIR, a pulsed beam, an epi-illumination system in which light is reflected by a half-silvered mirror through a dark field/bright field lens, and a dark field condenser lens. The light source may include means for separately with field with light having different excitation wavelengths.

The optical detector may include structure for spectrally separating light emitted from the PREs. The detector in this embodiment operates to form a computer image of the positions and emission spectral characteristic values of individual PREs and such other light-scattering entities present in the field at each of a plurality of different emission wavelengths.

The optical detector may include a two dimensional array of optical fibers, a grating or prism for responding to the output of the optical fibers when aligned to act as a line source of light from the array, and a two-dimensional detector array for responding to the spread-out spectral light from each fiber in the line source of light.

The image processor may operate to construct an image of field positions and associated values of peak position, peak intensity, or peak width at half intensity of the spectral emission curve, peak halfwidth in the image plane, and/or polarization or angle of incidence response.

In other embodiments, where the PREs have surface associated fluorescent or Raman-active molecular entities, the image processor operates to construct an image of field positions and fluorescence peak of plasmon-resonance induced fluorescence, or a Raman spectral feature in plasmon-resonance induced Raman spectral emission.

The discriminator may operate to discriminate a selected type of PRE from all other light-scattering entities in the field, PREs from non-PRE subwavelength light-scattering particles, including: (i) PREs from non-PRE light-scattering entities, (ii) one selected type of PRE from another, and (iii) PREs that are interacting through proximity effects from non-interacting PREs (typically PRPs).

The information displayed by the apparatus may be related to information about (i) the total number of PREs of a selected type in a field, (ii) the spatial pattern of PREs having a selected spectral characteristic in the field, (iii) a distance measurement between two adjacent PREs, particularly PREs separated by a distance less than the Rayleigh distance, (iv) a change in the environment of the field, e.g., dielectric constant, that affects a plasmon resonance characteristics, or (v) motion of PREs in the field.

In another aspect, the invention includes a composition of plasmon resonant particles (PRPs) having one or more populations of PRPs. The composition is characterized by: (a) the PRPs have a width at halfheight of less than 100 nm; (b) the PRPs in a single population are all within 40 nm of a defined wavelength; (c) at least 80% of the PRPs in the composition satisfying criterion (a) are in one or more of the populations and have a spectral emission wavelength in a single range >700 nm, 400-700 nm, or <400 nm; and (d) each population has at most a 30% overlap in number of PRPs with any other population in the composition. The composition may be used in practicing the above target-interrogation method, and/or in conjunction with the above target-interrogation apparatus.

In one embodiment at least 80% of the PRPs in the composition are in one or more of the populations and have a spectral emission wavelength in the 400-700 nm wavelength range. Also in this embodiment, the particles have a composition formed of a solid silver particle, a silver particle with a gold core, or a particle with a dielectric core and an outer silver shell of at least about 5 nm.

In one general embodiment, for use particularly in a variety of diagnostic applications, the particles have localized at their surfaces, (i) surface-attached ligands adapted to bind to ligand-binding sites on a target, where the ligand/ligand-binding sites are conjugate binding pairs, (ii) fluorescent molecules, (iii) Raman-active molecular entities, and (iv) a blocking reagent to prevent non-specific binding, (v) a coating with functional groups for covalent coupling to the PRPs, or (vi) combinations of (i)-(v).

The localized ligand may be one of a conjugate pair, such as antigen/antibody, hormone/receptor, drug/receptor, effector/receptor, enzyme/substrate, lipid/lipid binding agent and complementary nucleic acids strands.

The composition may have first and second populations of PRPs having first and second different surface localized molecules or entities. For use in identifying a target having first and second ligand-binding sites, the first and second surface bound molecules are first and second ligands effective to bind to the first and second ligand-binding sites, respectively. As an example, the first and second surface-localized molecules are oligonucleotides having sequences that are complementary to first and second proximate sequence regions of a target polynucleotide. As another example, the first and second surface-localized entities may be Raman-active molecular entities with different Raman spectral characteristics.

The composition may contain first and second populations of PRPs, each with a different shape, at least one of which is spherical or tetrahedral.

In still another aspect, the invention includes a diagnostic method for use in detecting the presence of, or information about, a target having a molecular feature of interest. The method includes contacting the target with one or more PREs (preferably PRPs) having surface localized molecules, to produce an interaction between the molecular feature and the localized molecules, illuminating the target with an optical light source, and determining the presence of or information about the target by observing a plasmon resonance spectral emission characteristic of one or more PRPs after such interaction with the target. The diagnostic methods may be carried out, for example, by the above target-interrogation method above, using the above target-interrogation apparatus.

In a general embodiment, the target contains a ligand-binding site, and the surface-localized molecule is a ligand capable of forming a ligand/ligand-binding complex with the target. The binding interaction is detected by detecting a plasmon resonance spectral emission characteristic of the complex. The surface localized ligand may be, for example, a polynucleotide, oligonucleotide, antigen, antibody, receptor, hormone, enzyme, or drug compound.

In a solid-phase format of the method, the target is washed to remove PRPs not bound to the target through a ligand/ligand-binding interaction, before detecting complex.

In a homogeneous phase of the method, the interaction of the PRE(s) with the target is effective to produce either a plasmon-resonance spectral emission characteristic which is distinguishable from that of the non-interacting PREs, or separate diffraction centers, where the two PREs have different peak wavelengths. By detecting one of these features, the presence of the diagnostic interaction can be determined.

In one homogeneous-phase embodiment, the PRE(s) contain surface-localized fluorescent reporter molecules, and the interaction of a PRE with the target or with another PRE at the target is effective to detectably alter a plasmon-resonance induced spectral emission characteristic of the fluorescent molecules on the PRE.

In another embodiment, the PRE(s) contain surface-localized Raman-active molecular entities, and the interaction of a PRE with the target or with another PRE at the target is effective to detectably alter a plasmon-resonance induced spectral emission characteristic of the Raman-active molecular entities on the PRE.

In still another embodiment, the target has two or more proximately spaced ligand-binding sites, and the complex that forms includes at least two proximately spaced PREs that have a spectral emission signature different from that of PREs in the absence of binding to the target, e.g., a change in the spectral emission curve of the complex, where the two PREs have substantially the same peak wavelength. Alternatively, where the two PREs have different peak wavelengths, the individual PREs may be interrogated at the two different wavelengths, and the distance between PREs determined by the distance between centers of the two diffraction patterns in the image plane. The embodiment may be practiced, for example, by reacting the target with first and second populations of PREs having surface-localized first and second ligands, respectively, for binding to the first and second ligand binding sites, respectively.

For use in forming a spatial image of the target, where the target has multiple ligand-binding sites, contacting the PREs with the target produces binding at multiple sites. The detecting step includes constructing a spatial image of the sites of PRE attachment to the target, which is indicative of the relative spacings of the ligand-binding sites in the target.

One application involves the mapping of closely spaced regions in a polynucleotide, where the detecting includes observing the spacing between centers of the diffraction patterns of the PREs in the image plane of the PREs.

Another application involves gene mapping, e.g., by binding PREs with different complementary surface-localized oligonucleotides to a target polynucleotide, with such in an extended condition.

In another embodiment, for use in detecting target sequence mutations or for sequencing by hybridization, the target is an array of different-sequence oligo- or polynucleotides. The array is contacted with one or more PREs having one or more surface-localized test polynucleotides, under conditions which allow the PRE's surface-localized polynucleotides to hybridize with the target array oligo- or polynucleotides. After washing the target to remove unbound PREs, a spectral emission characteristic of PREs at each region of the array is detected, to determine the pattern of polynucleotide binding to the array.

In another embodiment, the target is a polynucleotide present as a separated band in an electrophoresis gel, and the contacting is carried out by exposing the surface of the gel to PREs under hybridization conditions. This method simplifies the Southern hybridization method by eliminating a DNA band transfer step.

In another general embodiment of the method, the molecular feature of interest is a molecule which functions catalytically to break a bond between two atoms in a molecular chain. The PRE reagent in the method is a pair of PREs linked by said chain, where the linked PREs may have a spectral emission spectrum different from that of the individual, i.e., separated, PREs. The contacting is carried out under conditions effective to cleave the molecular chain. The presence of the cleaving agent is detected by the disappearance of the linked-PRE spectral emission signature, or the appearance of the individual-PRE spectral emission characteristic, or a change in the detected distance between the two PREs.

In another aspect, the invention includes a composition of plasmon resonant particles (PRPs) characterized by: (a) the PRPs have a width at halfheight of less than 100 nm; (b) at least 80% of the PRPs in the composition satisfying criterion (a) are in one or more of the populations and have a spectral emission wavelength in a single range >700 nm, 400-700 nm, or <400 nm; and (c) surface localized ligands adapted to bind to ligand-binding sites on a target, where the ligand/ligand-binding sites are conjugate binding pairs, (ii) fluorescent molecules, or (iii) Raman-active molecular entities.

The invention further includes a variety of PRE compositions and methods discussed in Section VI of the Detailed Description of the Invention.

These and other objects and features of the invention will become more fully apparent when the following detailed description is read in conjunction with the accompanying drawings.

DETAILED DESCRIPTION OF THE PREFERRED EMBODIMENTS

I. Definitions

Figure 1:
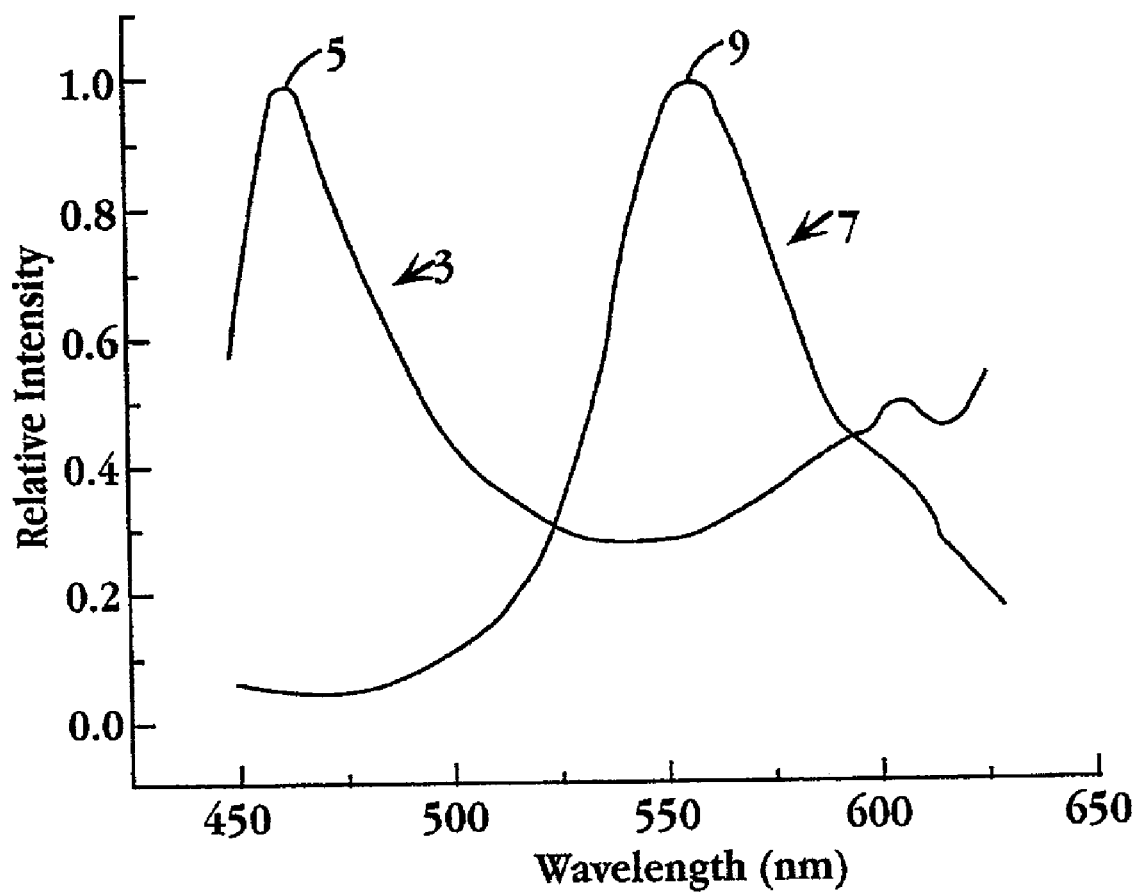
FIG. 1 is a graph of the relative scattering intensity of two optically observable plasmon resonant entities with disparate peak scattering wavelengths.

The following terms have the definitions given below, unless indicated otherwise:

"Plasmon resonant particle" or "PRP" denotes a single piece or fragment of material, e.g., spherical particle, which elicits plasmon resonance when excited with electromagnetic energy. A plasmon resonant particle can be "optically observable" when it exhibits significant scattering intensity in the optical region, which includes wavelengths from approximately 180 nanometers (nm) to several microns. A plasmon resonant particle can be "visually observable" when it exhibits significant scattering intensity in the wavelength band from approximately 400 nm to 700 nm which is detectable by the human eye. Plasmon resonance is created via the interaction of incident light with basically free conduction electrons. The particles or entities have dimensions, e.g., diameters preferably about 25 to 150 nm, more preferably, about 40 to 100 nm.

The term "plasmon resonant entity" or "PRE" is used herein to refer to any independent structure exhibiting plasmon resonance characteristic of the structure, including (but not limited to) both plasmon resonant particles (PRPs) and combinations or associations of plasmon resonant particles as defined and described above. A PRE may include either a single PRP or an aggregate of two or more PRPs which manifest a plasmon resonance characteristic when excited with electromagnetic energy.

A "field having a plurality of PREs distributed therein" is a one-, two-, or three-dimensional region, for example, a target or portion or region of a target having PREs attached or otherwise distributed therein, such that the PREs in the field, when illuminated with an optical light source, exhibit plasmon resonance.

A "spectral emission characteristic" refers to a spectral scattering characteristic of a PRE related to the plasmon resonance of the PRE, as discussed in Section III. As used herein, "emission", as applied to PREs, means scattered light produced or excited by plasmon resonance.

The "value" of a spectral emission characteristic is the qualitative or quantitative value of the emission feature, e.g., the value of the detected peak intensity, peak wavelength, or peak width at half maximum.

A "selected spectral signature" refers to a selected range of values of a selected spectral emission characteristic, e.g., a range of spectral peak intensity values.

A "computer image of the positions and values of the emission spectral characteristic" refers to a matrix which associates each region in a field being interrogated with one or more spectral emission characteristic values or signature measured for a light-scattering entity in that region. The image may be a matrix of stored values, or may be an actual image showing the locations of light-scattering entities in one dimension or plane, e.g., the x-y plane, and the associated spectral emission value in another dimension, e.g., the z-axis.

A "ligand" is a chemical species, typically a biochemical species, that is capable of forming a specific, typically high-affinity bond with a "ligand-binding" site or molecule. The ligand/anti-ligand form a conjugate pair that can include, for example, antigen/antibody, hormone/receptor, drug/receptor, effector/receptor, enzyme/substrate, lipid/lipid binding agent and complementary nucleic acids strands.

A "Raman-active molecular entity" is a molecule, molecular complex, or particle, e.g., silicon particle, that displays a Raman spectroscopic signature, preferably through resonance Raman excitation, when excited by electric fields of a plasmon-resonating particle to which the molecular entity is attached.

"Surface-localized" ligands and other species refer to molecular species that are attached to a PRE by covalent or other molecular forces, e.g., electrostatic or dispersion forces, or which are embedded in a shell or other surface coating on a PRE.

II. Plasmon Resonance

The present invention utilizes one or more of a number of spectral emission characteristics of conductive plasmon-resonance particles (PRPs or PREs) to interrogate a field for a variety of types of information, including the presence or absence of a target, spatial features of a target, the environment of a target, number and/or spatial distribution of a selected type of target binding sites, and distance relationships in the target, as will be detailed in Sections III-VI below.

Plasmon resonant entities (PREs) or plasmon resonant particles (PRPs) scatter incident light, and the resulting scattered light has a frequency spectrum characteristic of the particle. A general theory describing the interaction of an incident electromagnetic wave with a spherical particle which successfully predicts this resonant scattering was developed early in the 20th century (H. C. Van Ve Hulst, Light Scattering by Small Particles, Wyley, N.Y., 1957). In a metallic sphere, the incident electromagnetic field induces oscillations, referred to as "plasmons", in the nearly free conduction electrons of the metal, and these plasmons produce an emitted electromagnetic field. For some materials, and for the optimum choice of particle size, shape, and morphology, there will be a maximum scattering efficiency at a wavelength characteristic of the scattering particle and its surrounding medium. For some materials, the intensity of the emitted light is sufficient for observation under an optical microscope. Silver particles are the most notable exhibitors of this effect, as the wavelength of the resonantly scattered light can be in the visible region of the spectrum.

Theoretical calculations correctly predict that the resonantly scattered wavelength of a spherical particle will increase, or be "red-shifted", with increasing particle diameter and with increasing dielectric constant of the surrounding material. For spherical particles, dipole resonance produces a scattered frequency spectrum having a single peak at a wavelength which is dependent on the material the particle is made from, the size of the particle, the shape of the particle, the morphology of the particle, and the local environment. Larger particles have a longer dipole scattering peak wavelength, and smaller particles have a shorter dipole scattering peak wavelength. The spectrum of scattered light may also contain contributions from a particle's quadrupole resonance. For a given shape, a resonant particle scatters predominantly in a particular wavelength band depending on the composition and size of the particle.

The conductive portion responsible for the plasmons can take many different forms, including solid geometric shapes such as spheres, triangular parallelpipeds, ellipsoids, tetrahedrons, and the like, or may comprise spherical, cylindrical, or other shape shells. It is also true that a dielectric sphere of similar dimensions, having silver or gold on its surface will also exhibit plasmon resonances, assuming the shell has a thickness of at least about 3 nm, preferably 5 nm or more.

It can further be appreciated that contact or near contact between two plasmon resonant particles will produce an electromagnetic coupling between the particles, thereby producing an entity with properties in some ways similar to a single particle having a size equal to the sum of the two particles in contact. Aggregations of many plasmon resonant particles can therefore also exhibit plasmon resonance with characteristics dependent on the geometry and nature of the conglomerate.

Another feature of plasmon creation in a metallic particle is the generation of enhanced electric fields in the region near its surface. Interactions between this electric field and nearby materials can significantly alter both the scattering characteristics of the resonant particle and the nearby material. For example, Surface Enhanced Raman Spectroscopy (SERS) exploits the localized plasmon resonance in roughened or particle coated silver films to enhance the Raman scattering of various materials by as much as six orders of magnitude. In this technique, Raman scattering from the materials of interest is observed, and the local field generated by the plasmon is used to enhance the intensity of that scattering.

Referring now to FIG. 1, a graph of the relative scattering intensity of two PRPs is illustrated, demonstrating that different PREs can have differences in spectral characteristics that are easily detected. Although the spectra shown in FIG. 1 could be produced by either individual PRPs or PREs of a more complex structure, it will be assumed that the source of the scattered light spectra illustrated in FIG. 1 is from PRPs for explanatory purposes.

In FIG. 1, the relative intensity of scattered light in arbitrary units is plotted against wavelength in nanometers. The individual spectra of two different PRPs are shown—one, spectrum 3, having a peak emission 5 at approximately 460 nm, and a second, spectrum 7, having a peak emission 9 at approximately 560 nm. In this figure, the light intensity of the light emitted by each of the two PREs were individually normalized to 1.0. The shape of each spectrum is approximately Lorentzian, with a width at half maximum of approximately 30 nm for the particle with 470 nm peak, and approximately 50 nm for the particle with 560 nm peak. As has been mentioned above, the light emitted by individual PRPs can be visually observed with an appropriate optical microscope. If the two PRPs with emission spectra illustrated in FIG. 1 were so observed, the PRP with peak 5 at 470 nm would appear blue, and the PRP with peak 9 at 560 nm would appear yellow.

Figure 2:
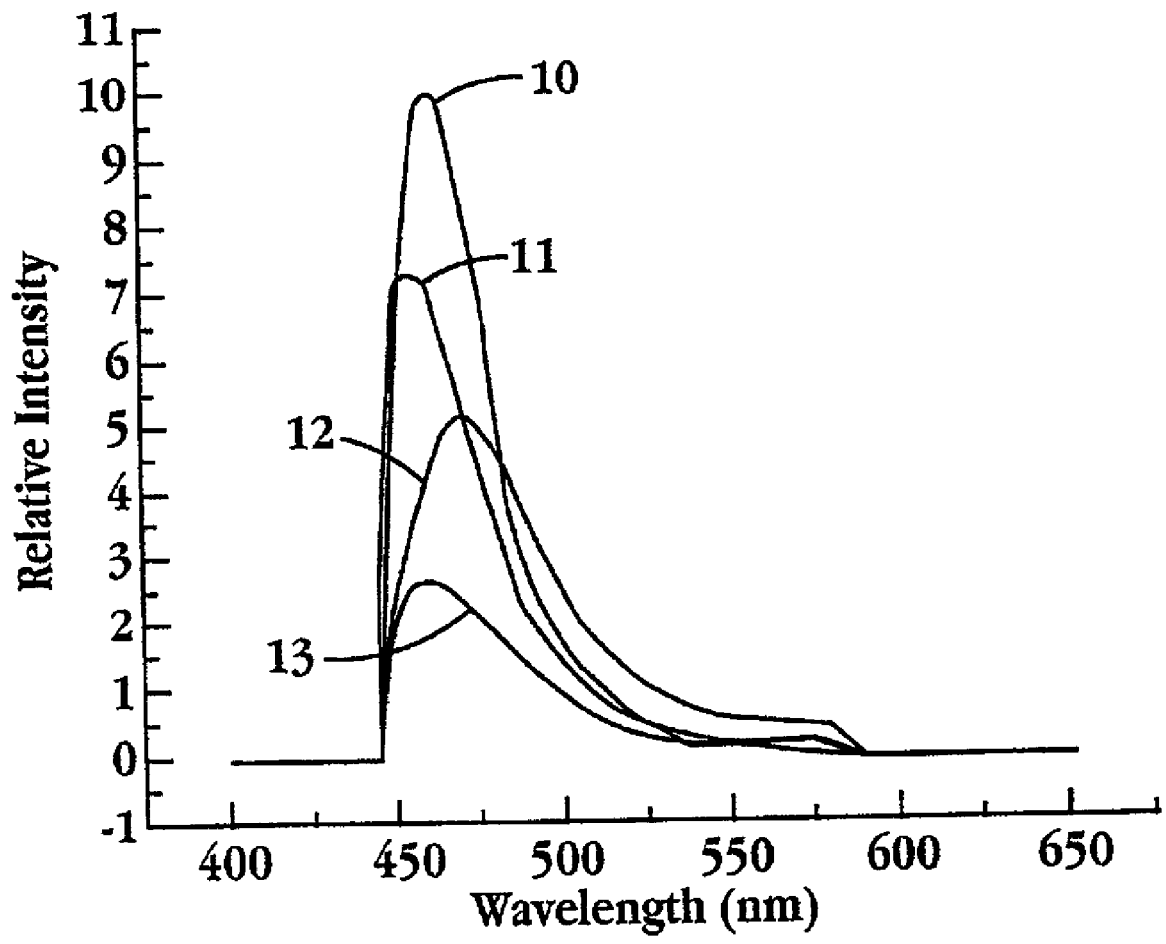
FIG. 2 is a graph of the relative scattering intensity of four optically observable plasmon resonant entities with similar peak scattering wavelengths.

FIG. 2 shows the spectral emission curves for a population of four different populations of PREs, each having an approximately homogeneous properties. The spectra 10, 11, 12, 13 of the four PREs shown in this figure have peak emission wavelengths which vary from approximately 460 nm to 480 nm. Visually, each of the four PREs which produce the spectra shown in FIG. 2 would appear blue in color. The four particles can be distinguished, however, on the basis of spectral peak intensity, i.e., peak height, or on the basis of the different spectral emission curves, for example, by comparing the ratios of peak height to peak width at half peak height. Other spectral emission characteristics are discussed below.

III. Method and Apparatus for Interrogating a Field

In one aspect, the invention is directed to a method and apparatus for interrogating a field having a plurality of PREs distributed therein. The method has three parts, in essence: (i) generating data about one or more spectral emission characteristic(s) of PREs in the field, (ii) from this data, constructing a computer image of the PRE positions (regions in a field) and values of the emission spectral characteristic of individual PREs and other light-scattering entities present in the field, and (iii) by discriminating PREs with selected spectral characteristics in the image from other light-scattering particles in the field, providing information about the field, e.g., a target in the field.

A. Spectral Emission Characteristics

The invention contemplates detecting one or more of several types of spectral emission characteristics, for generating an image of light-scattering particles in the field. The spectral emission characteristics of interest may be plasmon-resonance spectral features of a single PRP, a shift in spectral emission feature due to the interaction of two or more PRPs in close proximity, or a fluorescent or Raman spectroscopic feature induced by the enhanced local electric fields interacting with fluorescent, luminescent, or Raman molecules localized on PREs. The most important of characteristics, and the type of information available from each, are the following.

Peak wavelength is the wavelength of the peak of the spectral emission curve, that is, the wavelength at which maximum intensity occurs. Peak wavelengths for the two spectral emission curves shown in FIG. 1 are indicated at 5 and 9, corresponding to wavelength values of 470 nm and 560 nm, as described above.

The peak wavelength value can be determined in one a number of different ways, seven of which are described here. The implementation of each of the methods will be understood from the disclosed method, and for some of the methods, as discussed below in the description of the light source and detector in the apparatus of the invention. All of these methods are applicable to measuring the spectral curves for a plurality simultaneously. It will be appreciated that some of the methods are also applicable to measuring the spectral curve of each light-scattering entity in the field individually, for example, by rastering a photodetector element over the plane of the field.

(i) The field is illuminated over a range of illuminating wavelengths, for example, at each of a series of narrowband illumination windows through the visible light spectrum. Typically, a filter wheel interposed between a white light source and the field is employed to generate the narrowband illumination frequencies.

(ii) Light emitted from the field is directed through a dispersive element, such as a prism, for breaking the emitted light into several narrowband frequencies, which are then each directed to a separate detector array. As an example, a prism is used to break the emitted light into red, green and blue components, each directed onto a separate CCD array.

(iii) Take the emitted field image into a dense bundle of optical fibers, through a lens that, for example, magnifies each light-scattering spot corresponding to a PRE, such that its image fits entirely in the core diameter of an optical fiber. Each fiber is then broken up by a dispersion element into spread out spectrum line of different frequencies, which is then read by a line of detector elements in a two dimensional array. Thus each line in the field is read by a 2-dimensional array, one array dimension corresponding to the spectral intensity at each of a plurality of frequencies, and the other dimension, to different positions along an axis in the field. This approach allows for simultaneous reading of a plurality of PREs at each of a plurality of spectral wavelengths.

(iv) Illuminate with multiple narrow band light sources, e.g., 3 or 4 separate laser lines in the red, green, yellow and blue. Each laser is chopped at a different frequency, typically all under 100 Hz. The emitted light from the field is detected in a CCD that can be read at 100 frames/sec. Computer analysis involving standard techniques is then used to determine the amount of light of each color impinging on each pixel in the CCD array, thereby allowing the spectral emission curve to be constructed.

(v) The same information may be obtained by routing the scattered light through an interferometer, as described for example, in U.S. Pat. No. 5,539,517.

(vi) It is also a property of plasmon resonant particles that the scattered light undergoes a 180 degree phase shift relative to the incident light as the wavelength of incident light is swept through the resonant peak. At the peak wavelength, the phase difference is 90 degrees. This phase shift can be detected, and the peak scattering wavelength can be determined as that incident wavelength when a phase shift of 90 degrees is observed.

(vii) The intensity of PRE light emission at a plurality of defined bandwidths can also be determined by exposing the PREs to short pulses of incident light of varying duration. In particular, it is effective to use pulses approximating a step function increase or decrease, that is, with fast rise time or decay time of only 1 or 2 femtoseconds. The scattering response of a PRE is that of a forced and damped oscillator, and near the resonant wavelength, the response of a PRE to narrowband excitation increases as the excitation pulse length increases. Away from the resonant wavelength, the response to narrowband excitation is small, and relatively independent of the excitation pulse length. Exposing a PRE to pulses of varying duration, but all advantageously less than about 500 femtoseconds, at a particular wavelength and noting how long it takes for the emitted energy to reach a steady state value provides information about how close that particular wavelength is to the PRE resonant wavelength. By exciting the PREs to several series of duration variable pulses, wherein each series has a different peak wavelength, a curve of scattering cross section versus wavelength can be generated.

The peak wavelength generally shifts toward the red (longer wavelengths) as the size of the PRE increases for silver and gold PREs. Peak wavelength values can also provided information about PRE shape. Shape changes from spherical to hexagonal or triangular result predominantly a shift of peak wavelength toward the red. Dielectric-shell PRPs, i.e., particles composed of an inner dielectric core encased in a conductive metal also tend to have longer peak wavelengths than solid metal particles of the same size.

Peak intensity is the intensity of the peak of the spectral emission curve, and may be expressed as an absolute or relative intensity value, as in FIG. 2, which shows four PREs with different relative peak intensities ranging from less than 3 to greater than 10. The peak intensity value is determined, as above, by one of a variety of methods for determining the spectral emission curves of the PREs, with intensity being determined at the peak wavelength.

The peak intensity will vary with material, morphology and shape. For a particular PRE, the intensity will be a maximum in the pane of focus.

Width at half peak height is the width, in wavelength units, of the spectral emission curve at half peak intensity. This value may be measured as an independent spectral characteristic, or combined with peak spectral intensity to characterize the spectral emission curve, for example, the ratio of peak intensity/peak width.

The four curves shown in FIG. 2 illustrate two spectra with relatively narrow peak widths (curves 10 and 11), and two with relatively broad peak widths (12 and 13).

Generally peak width increases with increasing size of the PRE, and changes as the shape of the PRE changes from spherical to non-spherical shapes in a manner which can be simulated.

Width in the image plane is the halfwidth of the central diffraction region in the Airy pattern in the image plane. All PRPs are sub-wavelength sources of light, and so their spatial image will be an approximate point spread function with characteristics defined by the optical system being used. Assuming that the optical system includes a CCD, with a pixel array of photodetecting elements, the width of the central diffraction region, which may cover several pixels, is measured radially from the peak of the center of the diffraction image to the position in the center of the image where the intensity has fallen to half its peak value (assuming a circular image).

Since the PRPs are subwavelength scatterers, the halfwidth of the intensity pattern as recorded in the image plane will be proportional to the wavelength of light being scattered. Therefore, for a reasonably smooth variation in light intensity from a source (such as a Xenon arc), the light is scattered most strongly is at peak intensity, and one can make a good estimate of peak wavelength by measuring the width of the half intensity of the central diffraction region in the image for each PRP.

As will be seen below, this spectral characteristic is useful for precise determination of the positions of PREs in a field, and particularly for determining the distance between two PREs of different peak wavelengths that are more closely spaced than the Rayleigh resolution distance. The intensity of the peak of the diffraction pattern in the image plane can be used for focusing the detector lens on the field, with the maximal value giving the best focus.

Polarization measures a spectral characteristic, e.g., peak wavelength, peak height, width at half wavelength, or width at half peak intensity in the image plane, as a function of direction of polarization of light illuminating a PRE field, or the angle of incidence of polarized light. The polarization characteristic depends on PRE shape rather than size, and is due to the fact that a non-spherical PRE may have more than one resonance, for example, along the directions of the major and minor axes in an elliptical PRE. In the latter case, illuminating light directed along the major axis would be shifted toward the red, while that directed along the minor axis, would be shifted toward the blue.

Pulse or time response provides a measure of the number of light cycles of the illuminating light that are required to "pump up" the scattering to full intensity. PREs have very fast time response (sub-picosecond), and very large pulses of scattered photons can be generated, the only limitation being the average input power absorbed. They can accept pulses between 5 to 500 femtosecond for driving two-photon processes or second harmonic generation and other higher order processes.

As noted above, pulsed or timed illumination measurements are generally made by exposing PREs in the field to short pulses of incident light of varying duration, to detect peak wavelength. The time to full resonance, as measured by intensity versus pulse time, also provides a measure of the quality of the material as a plasmon resonator. Higher quality material is characterized by a narrower width of the resonance signature, a higher peak intensity, and a longer time to reach the maximum intensity of scattering when illuminated by pulses of light at the peak wavelength.

Phase shift is discussed above in the context of determining spectral peak at 90 degree phase shift. Phase shift can also give information about the response for excitation wavelength away from the resonant peak wavelength.

Fluorescence emission lifetime can be observed in PRE particles having surface-localized fluorescent molecules. The fluorescence excitation can be enhanced by the local electric fields generated near the surface of the PRE by light within the plasmon resonance peak. Fluorescence emission can also be enhanced if the wavelength of the fluorescence emitted light is within the plasmon resonance peak. Under appropriate conditions, the fluorescence lifetime can be measurably shortened in this process.

The method can be used to detect changes in the excitation environment of the fluorescent molecules, e.g., proximate interactions with other molecules or entities.

Surface enhanced Raman scattering (SERS) relies on the generation of enhanced electric fields in the region near the surface of a PRE. Interactions between this electric field and nearby materials can significantly alter both the scattering characteristics of the resonant particle and the nearby material. Surface Enhanced Raman Spectroscopy (SERS) traditionally exploits the localized plasmon resonance in roughened or particle evaporated silver films to enhance the Raman scattering of various materials by as much as six orders of magnitude. The SERS performed in accordance with the present invention is confined solely to PREs. In this technique, Raman scattering from the materials of interest is observed, and the local field generated by the plasmons is used to enhance the intensity of that scattering by many orders of magnitude over traditional SERS. When the Raman active molecule has a resonant absorption near peak of the spectral emission curve of the PRE, the additional SERS enhancement is sufficient to make the Raman signal of the PRE-molecule composite detectable, in accordance with the method of the invention disclosed in Section III. Measuring changes in the PRE resonant Raman spectrum can be used to detect alterations, e.g., binding, in the local environment of the Raman molecule.

B. Field to be Interrogated

The field that is to be interrogated, in accordance with the method and apparatus of the invention, includes a target or target region having a plurality, i.e., two or more PREs distributed in the target.

The target may be any target that is suitable for viewing by light microscopy, including biological cells or tissues; plant or animal parts or cellular aggregates; a solid surface having surface-localized ligand-binding molecules; a fluid sample containing target analyte molecules, particles or cells; biological sample material, such as chromosomal material placed in an extended condition; artificial monolayer or bilayer membrane substrates; a microfabricated device, such as an computer microchip; and a microarray, such as a microarray of oligonucleotide or oligopeptides on a chip.

Methods for forming PREs and preparing a target having PREs distributed therein will be discussed in detail below. At this point, three general cases will be briefly considered. First, preformed PREs are added to a target, for attachment at specific target sites. The target may be washed to remove unbound or non-specifically bound PREs. The target may be manipulated before or after PRE binding to achieve a desired configuration, e.g., an elongated chromosome. Second, nucleation sites may be added to the target. After binding to selected locations on the target, a metal enhancer solution, e.g., silver solution, is added until an appropriately sized PRE is formed. In the third case, PREs are formed by photolithographic methods, e.g., photomasking and photoetching, on a metal substrate, e.g., silver substrate.

The types of information which one wishes to determine, by interrogating the field containing the target and PREs, in accordance with the invention include: (i) the total number of PREs of a selected type in the field, (ii) the spatial pattern of PREs having a selected spectral characteristic in the field, (iii) a distance measurement between two adjacent PREs, particularly PREs separated by a distance less than the Rayleigh resolution distance, (iv) a change in the environment of the field, e.g., dielectric constant, that affects a plasmon resonance characteristics, (v) motion of PREs in the field, (vi) whether two PREs are linked, or (vii) a fluorescence or Raman emission of molecules or materials attached localized on PREs. Other types of information, are also contemplated, and will be considered in Sections IV-VI below.

C. Apparatus of the Invention

Figure 3:
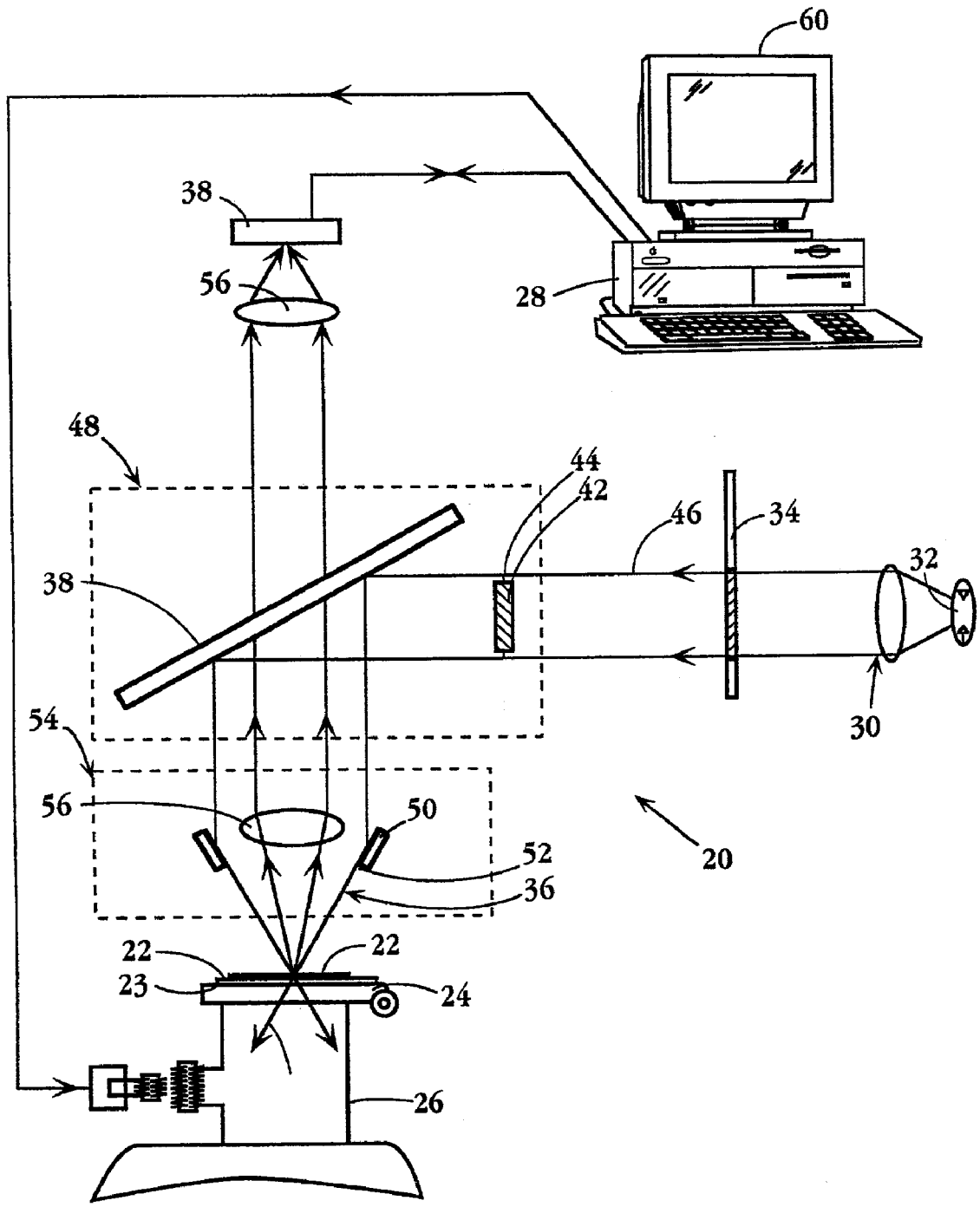
FIG. 3 is a schematic illustration of one embodiment of a darkfield microscope detection system suitable for the observation of plasmon resonant entities.

FIG. 3 is a simplified, schematic view of an apparatus 20 constructed in accordance with the invention. The target to be interrogated, here indicated at 22, is supported on a substrate 23 held on a microscope stage 24 which is selectively movable in the x-y plane under the control of a stage steppermotor device, indicated generally at 26, under the control of a computer 28, which includes other computational components of the apparatus as described below.

The target is illuminated by an optical light source 30 which directs illuminating light, typically light in the visible range, and at one or more selected wavelength ranges, onto the target surface. As will be detailed below, the light source typically includes a means 32 for generating light of a given wavelength or spectral frequency, one or more filters, such as filter 34, for producing a desired frequency band of illuminating light, and a lens system 36 for focusing the light onto the target, in a manner to be detailed below.

Spectral emission light from the target, in this case light scattered from the target, is directed through lens 56 to an optical detector 58. The optical detector functions, in a manner to be detailed below, to detect one or more spectral emission characteristics of the individual PREs in the illuminated portion of the field. The detector is typically a CCD (Charge Coupled Device) array which operates to generate and store an array of optical intensity values corresponding to the array pixels, as will be detailed below.

An image processor contained within computer 28 is operatively connected to the detector to receive values of light intensity at each of the detector array positions, under each selected illumination condition, e.g., different wavelength or polarization state. The image processor functions to construct a computer image of the positions and values of one or more spectral emission characteristics measured by the detector. Typically, this is done by treating each pixel in the detector array as a position point in the illuminated field, and assigning to each pixel "position" the light intensity value recorded by that pixel. The image generated by the image processor may be a matrix of stored numbers, e.g., position coordinates and associated spectral emission characteristic value(s), or an actual map in which position are represented, for example, in an x-y plane, and each measured spectral emission value, represented as a quantity along the z axis, for each pixel location.

A discriminator 42 in the apparatus, also forming part of computer 28, functions to discriminate PREs with a selected spectral signature, i.e., a selected range of values of one or more selected spectral emission characteristics, from other light-scattering entities in the computer image. Examples of the operation of the discriminator will be given below.

C1. Substrate

As indicated above, the target is supported on a substrate which is mounted on a microscope stage. Suitable substrates include standard glass slides, cover slips, clear polystyrene, and clear mica as examples. Other suitable transparent substrates are those associated with a TEM grid, including for example, formvar, carbon and silicon nitride. These TEM-associated substrates are all optically transparent at the thicknesses used. Conducting, semiconducting, and reflecting substrates are also suitable for PRE applications.

Another suitable substrate for use in the present invention are those which may initially appear opaque to the spectral wavelengths of interest for PRE observation, but which can be rendered suitable by the application of a suitable fluid or vapor. An example is white nitrocellulose "paper" as used for the transference of biological samples of interest in diagnostic techniques such as "Southern", "Northerns", "Westerns", and other blotting, spotting, or "dip stick" tests. Once the materials of interest have been transferred and fixed as desired, the PRE's can be applied as preformed entities, or one can apply PRE nucleation entities and enhance as described below. The white nitrocellulose at this stage may typically present significant non-specular light scattering which makes it difficult to visualize the PREs. However, if a suitable treatment which results in a significant reduction of the non-specular scattering is used, for example, allowing acetone vapor to encompass the nitrocellulose substrate, while monitoring the PREs, the substrate can become much less opaque, and permit efficient observation of the PREs.

Silicon is a preferred substrate for many PRE detection applications because it can be made very smooth and free of defects, resulting in very little non-specular scattering under darkfield illumination. One example of a particularly preferred silicon substrate is the highly polished, etched, and defect free surfaces of silicon wafers commonly used in the manufacture of semiconductors. The nearly complete absence of contaminants and surface imperfections of such a substrate produces excellent contrast of the PRE scattering under darkfield illumination conditions. However, it should be appreciated that such silicon wafers typically have a thin layer of $SiO_2$ present on their surface as a result of the various processing steps. It may be mentioned that silicon substrates with approximately 100 nm or more of $SiO_2$ on their surface produce some of the most intense, high contrast PRE spectra so far observed from a solid substrate, and it may be advantageous to intentionally grow a sub-micron layer of $SiO_2$ on the silicon wafer surface.

If the oxide layer is removed from the silicon surface in a manner that prevents rapid re-growth of an oxide layer, for example, by etching in HF acid and passivating the surface with hydrogen, the optical image of the "point-source" PREs has been observed to be torus-shaped, rather than the usual Airy ring pattern with a bright central region. This "doughnut" phenomenon most likely arises as a result of damping of the transverse driving electric fields (those parallel to the silicon surface), leaving only the perpendicular driving fields which can excite a plasmon mode that radiates well, but not at all directly along the normal. This property of bare silicon substrates can be useful in determining whether a particular PRE is closely bound to the surface of the silicon substrate, or is bound via a tether molecule or system that has placed it further from the surface, thereby changing the dipole component scattering ratios.

C2. Light Source and Detector

With continued reference to FIG. 3, light-generating means 32 in the light source may suitably be a mercury, xenon, or equivalent arc; or a Quartz-tungsten halogen bulb, of approximately 20 to 250 watts, which provides incident light in a frequency band corresponding to wavelengths from approximately 350 nm to 800 nm, for visible light PRE scattering, or a conventional UV source for lower-wavelength PRE scattering.

Filter 34 typically includes a set of pre-selected narrow bandwidth filters, allowing manual or computer controlled insertion of the respective filters. The bandwidth for such filters is typically 5-10 nm.

Other methods of illuminating a target with a series of selected bandwidths include the use of light sources such as lasers of all types where one may utilize very narrow bandwidths. Multiple frequency sources are also contemplated, such as tuned lasers (i.e. Ar-ion) to select any of the characteristic defined strong "line" sources. Alternatively a grating or prism monochrometer can be used. All the light sources can be either of continuous or pulsed variety, or a suitable light amplitude modulation device (not shown) can be inserted in the incident path to vary the intensity level in a prescribed temporal manner. The polarization of the light to be incident upon the sample can be varied by the insertion of suitable filters or other devices well known to the art.

The microscope in FIG. 3 is illustrated to be configured with an epi-illumination system, whereby the collimated light from the source following filtering as desired impinges onto a half silvered mirror 38, and is reflected downwards towards the Darkfield/Brightfield (DF/BF) lens 40. In this particular type of DF/BF application, the incident light that would have had rays passing through the objective lens is physically blocked by an opaque circle 42, which is suspended by very fine webs 44, so as to allow only a concentric band of light to pass such as bounded radially and illustrated by the rays 46. The unit comprising mirror 38 and opaque circle 42 may be built into an adjustable block 48 that can be manually (or robotically) moved thereby converting the microscope from DF/BF to alternate forms of operation.

Light reflected from the mirror may in turn be refracted or reflected (by a suitable circular lens element 50, fixed to the objective lens mount into a hollow cone of incident light 52, converging toward a focus at the sample plane of the target. As previously noted, the specular reflection of such rays causes them to return along the lines of the incident cone trajectories, where they are ultimately absorbed or otherwise removed from the optical system.

In this darkfield system illustrated in FIG. 3, the angle between the optic axis and the incident rays illuminating the sample is larger than the largest angle between the optic axis and the rays scattered by the PREs which is accepted into the objective lens element 45, which is illustrated to be of the refractive form. Also incorporated in the total optical microscope, although not shown, is the ability to divert the light rays away from detector 38 to other ports whereby the image may be observed visually through standard binocular eyepieces, or to yet another port, for example, for photographing the illuminated field.

It has been found to be suitable to use a Nikon DF/BF lens model CF Plan BD ELWD with magnification 100× and numerical aperture (N.A.) 0.8 as the lens system 54, and also a model CF Plan BD ELWD with magnification 20× and N.A. 0.4. In that case, the rays entering the objective element of the lens may be rendered parallel and incident upon the 50% mirror 38, and into a relay lens 56 (typically magnification of 2× or 5×) that focus the rays to an image plane on detector (image capture device) 58, where the detection is performed by a suitable CCD camera system.

The optical system, including lens 56, is preferably constructed to project the field being viewed into an area corresponding to the array of the detector, so that each pixel in the array is reading light from a defined region of the field.

Various image capture devices known in the art may be used, including fiber coupled photo-diode arrays, photographic film, etc. One exemplary device is a thermoelectrically cooled CCD array camera system, model CH250, manufactured by Photometrics, of Tucson Ariz. This device utilizes a CCD chip model KAF1400, having a 1032 by 1037 pixel array.

It will be appreciated that the detector serves to detect a spectral emission characteristic of individual PREs and other light-scattering entities in the field, when the field is illuminated by the light source, simultaneously at each of the regions in the field corresponding to array pixels.

C3. Image Processing, Discrimination and Output

Where the detector is used, for example, to detect spectral peak wavelength, peak intensity, and/or half width of the spectral peak, the detector measures light intensity at each of a plurality of different illuminating light frequencies, simultaneously for each of the field regions corresponding to a detector array pixel.

The emission (scattering) values measured at each frequency are stored, allowing spectral emission curves for each region to be constructed after a full spectrum of illumination. From these curves, peak wavelength, peak intensity, and width at half intensity are calculated for each region. Similarly, the peak halfwidth in the image plane can be measured with a CCD array as described above.

The detector may be supplied with comprehensive software and hardware that allows timed exposures, reading out of the pixels into suitable files for data storage, statistical analysis, and image processing (as one of the functions of computer 28). This capability serves as an image processor for constructing from signals received from the detector, first the values of the spectral emission characteristic(s) being determined, and then a computer image of these values and the corresponding associated field positions.

The image constructed by the image processor may be a matrix of stored points, e.g., a matrix of associated values of each field position (regions in the field) and values for one or more measured spectral characteristics, or may be an actual map of field positions, e.g., in the x-y plane, and associated spectral emission values in the z plane.

The computer in the apparatus also provides discriminator means for discriminating PREs with a selected spectral signature from other light-scattering entities in the computer image. The basis for this discrimination is noted above in the discussion of various spectral emission characteristics and their correlation with physical properties of light-scattering entities.

Thus, for example, to discriminate PREs with a selected spectral peak wavelength and peak width at half intensity, the computer image generated could provide a matrix of all field regions and the associated spectral peak wavelength and width values. The discriminator would then selected those regions containing PREs whose spectral signature meets certain ranges of these two spectral emission values. Depending on the particular values chosen, the discriminator could classify light-scattering entities in the field in a number of ways, including distinguishing:

1. PREs with a selected spectral signature from all other light-scattering entities in the field;
2. PREs from non-PRE light scattering entities in the field;
3. For a selected type of PREs, those selected PREs which are interacting with one another and those which are not; and
4. One selected type of PRE from another selected type of PRE in the field.

Figure 11:
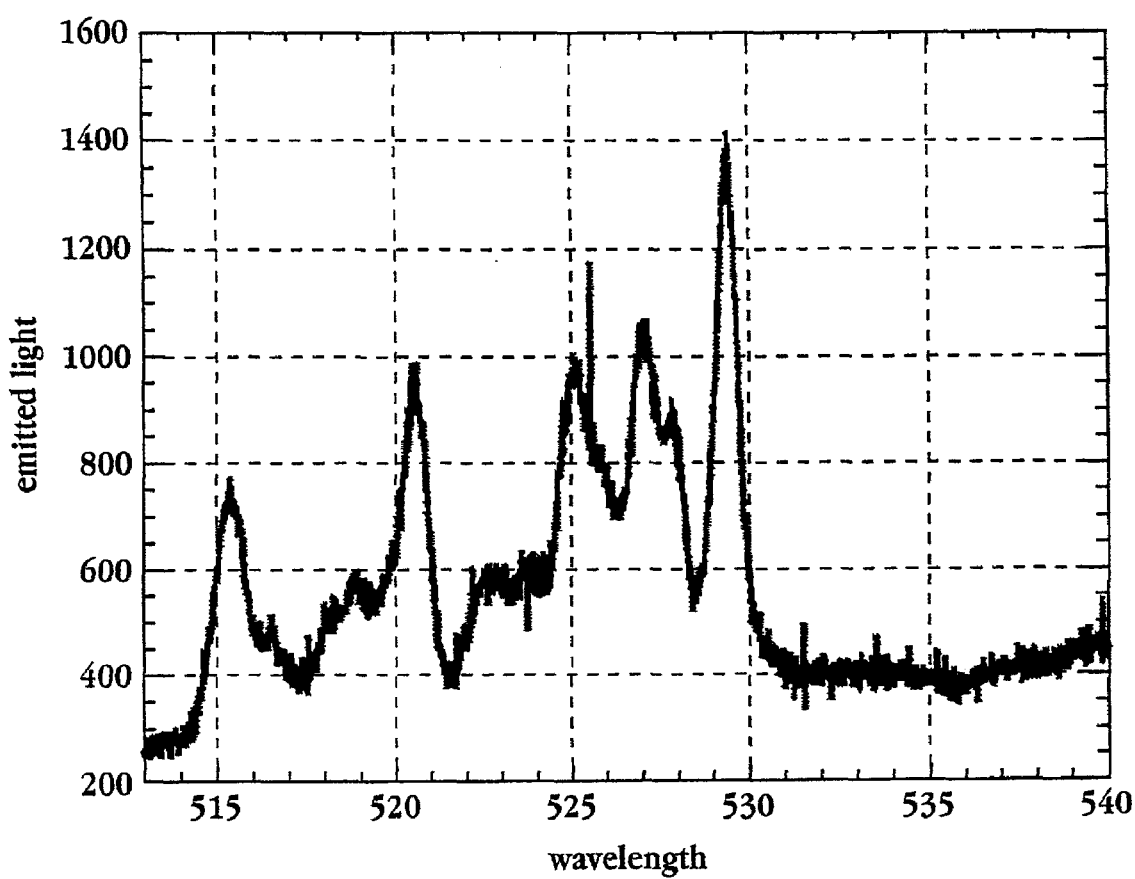
FIG. 11 is a Raman signature from a Raman-active PRE.

In each case, the basis for the discrimination may be based on detected values, for each light-scattering entity in the field, of peak position, peak intensity, or peak width at half intensity of the spectral emission curve, peak halfwidth in the image plane, and polarization or angle of incidence response. Other spectral characteristics mentioned above are also contemplated. In particular, where the PREs have surface-localized fluorescent molecules or Raman-active molecular entities, the detecting may detecting plasmon-resonance induced fluorescent emission or Raman spectroscopy emission from one or more of said molecules or entities, respectively, and these values are used as a basis of discriminating such PREs from other light-scattering entities. FIG. 11 shows a typical Raman spectrum of a Raman-active molecule carried on the surface of a PRE.

The information obtained from the discriminating step is then used to provide information about the field. Various types of information available are discussed in Sections IV-VI below. Among these are:

1. The total number of PREs of a selected type in a field. Here the discriminating step includes counting the number of PREs having a selected range of values of a selected spectral emission characteristic in the constructed computer image;

2. Determining a spatial pattern of PREs having a selected range of values of a selected spectral characteristic in the field. Here the discriminating includes constructing an image of the relative locations of PREs with those spectral-characteristic values;

3. The distance between two adjacent PREs, particularly where this distance is less than the Rayleigh resolution distance. Here the detecting includes exposing the field with light of one wavelength, to obtain a diffraction image of PREs in the field, exposing the field with light of a second wavelength to obtain a second diffraction image of PREs in the field, and comparing the distance between peaks in the two diffraction patterns;

4. Interrogating a change in the environment of the field. Here the discriminating includes comparing the values of the detected spectral characteristic of a PRE in the field before and after the change, e.g., change in the dielectric of the field;

5. Detecting motion of PREs in the field. The detecting here includes detecting the centers of the diffraction patterns of the PREs in the image plane, as a function of time.

C4. Other Embodiments

Simultaneous imaging of even 100 PRPs or more in the illuminated field may be readily and efficiently accomplished, using the apparatus just described. Alternatively, the apparatus may be designed to "read" a spectral characteristic of each PRE in a field by sequentially scanning each region in a field with a focused-beam light source, and/or sequentially detecting light scattering from each region in the field, by moving the microscope stage through a small interrogation region defined by stationary optics, sequentially interrogating each region to determine values of a selected spectral characteristics, according to above-described methods.

For detecting fluorescent images, the light source is filtered appropriately for the excitation spectrum of the desired fluorophore, and a suitable filter (not shown) is placed in the region between mirror 38 and relay lens 56. This filter is chosen to substantially block the excitation light and permit passage of light in a band matching the emission spectrum of the fluorophore(s) of interest.

The value of the ability to make comparison of the multiple images of darkfield PRP treated, brightfield dyed, and/or fluorescent stained samples such as cells and other entities of interest to biological and medical researchers and clinical applications can be readily appreciated.

There are several suitable means for bringing in the incident light so as to establish effective darkfield conditions in conjunction with suitable means for preferentially and efficiently observing the light scattered by the PREs. For transparent substrates the incident light may be brought in either in transmittance through the substrate, reflectance from the "objective side surface", or via TIR (total internal reflection) at the interface near which the PREs are situated, as shown in FIG. 3 and described in more detail below. In the latter case the evanescent tail of the TIR light may also be used to excite the PREs, if they are directly outside the reflecting interface, even though such light field distributions do not radiate directly to the objective lens.

For non-transparent substrates, the light must be incident in a manner that results in as near specular reflection as possible, with a minimum of such light reaching the objective. There are several means for accomplishing this condition. As one example, incident light may be routed to the field of view through one or more optical fibers. The fibers may be oriented such that light reflects off the substrate at a glancing angle and does not enter the objective lens of the microscope system used to image the PREs. It is also advantageous to use commercially available DF/BF objective lenses. Examples are those sold by the Nikon Company, Long Island N.Y. An example of the way such a DF/BF lens may be used is illustrated in FIG. 3.

The objective lens of system in the apparatus can be made as either a reflecting or refracting lens. For certain PRE applications, especially those requiring the most accurate and rapid focusing of the objective lens as a function of light wavelength, reflecting lenses may be preferred because chromatic aberrations can be greatly reduced. Refracting lenses, even those carefully made to compensate for chromatic aberrations when observing light emitted by PREs, can still exhibit significant deviation in their frequency dependence of the focal length. The fact that the PREs near the peak of their plasmon resonance can be of such extraordinary brightness for a sub-wavelength sized source allows them to be utilized for evaluation of optical components, whereby one can observe a variety of deviations from the component's ideal "point source" response.

The use of particular lens types which enhance the numerical aperture of the objective is also contemplated. PREs can be imaged with a standard "solid-immersion" lens having a spherical top and flat lower surface. Another such contemplated lens is a liquid analog to a solid immersion lens (SIL) having a fluid between the lower surface of a truncated solid immersion lens and a substrate which has an approximately equal index of refraction as the lens material.

Figure 4:
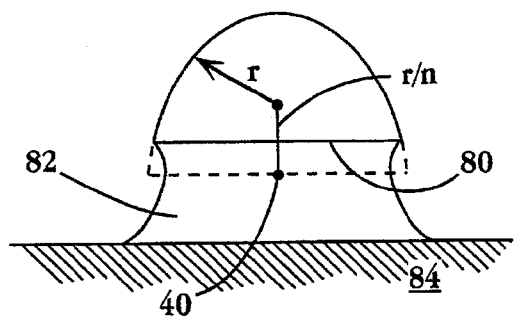
FIG. 4 is an illustration of a liquid analog to a solid-immersion-lens which may be used to observe plasmon resonant entities.

Such a lens is illustrated in FIG. 4. The lower flat surface 80 of the lens is cut shorter than a standard solid immersion lens. With the index matched fluid 82 between the lower surface 80 and a substrate 84, the focal plane of the lens is at the usual r/n (where n is the index of refraction of the lens material) location, which is now inside the index matched fluid. PRPs in the fluid at this focal plane are thus imaged with this system, allowing focusing on non-substrate bound PREs in solution. Such a lens can readily be added to a commercial DF/BF microscope lens by one of ordinary skill in the art, thereby resulting in an improved numerical aperture and increased magnification for viewing samples in a liquid matrix. In particular, this modification results in increased brightness and clarity in visualization of the PREs. This configuration allows the user to vary the focal position in a liquid sample while retaining a large numerical aperture and removes the usual requirement of total internal reflection-based illumination as is used for the SIL. This system therefore allows the monitoring of movement of a particular PRE in solution.

In other preferred embodiments, darkfield optics are chosen to optimize the signal to noise ratio of the PRE signal. This often includes improving the contrast by reducing the background (non-PRE) scattered light to a minimum, or to a minimum relative to the amount of PRE scattered light observed. For example, using ordinary 1"×3" glass microscope slides, it was determined that the Nikon DF/BF lenses of the extended working distance class had a better contrast for observation using the 0.8 NA lens compared to the 0.9 NA lens at the same magnification level (100×), despite the fact that the higher the NA of a lens the more scattered light is collected from the PRE. This may be attributed to the change in reflecting properties of the bare glass substrate since the angle of incidence of the darkfield illumination light is changed when the NA of the objective is changed.

Polarized incident light can also be used at specific angles (i.e. the Brewster angle) to reduce the amount of reflected light from the surface of the substrate. This improves contrast by reducing the amount of non-PRE scattered light which enters the objective lens. When imaging non-spherical PREs such as ellipsoidal PREs as described above, the response to plane polarized incident light can also be used to distinguish different PRE populations.

In another embodiment, a transparent substrate is used which is sufficiently thick so as to reduce the amount of light scattered from its bottom surface that reaches the detector. If particulates are present on the bottom surface of a thin glass substrate, some of the scattered incident light will re-enter the detection system and increase background. By increasing the thickness of the substrate, one displaces the region of the spurious scattering further from the optical axis, thereby reducing the amount of non-PRE scattered light that enters the detector.

Total internal reflection (TIR) may also be used to illuminate PREs in a transparent substrate from beneath. The evanescent tail of such light can be effectively used to excite the PRE located near that interface. There are several methods for exciting PREs with totally internally reflected light, such as using an optical fiber whose dimensions and indices of refraction of the inner core and outer layer are chosen so that there is sufficient evanescent field at the fiber outside surface to excite PREs placed thereon. The light emitted from the PRE can be transferred back to the fiber, forming a reflected source of light which can be observed by standard methods.

Figure 5:
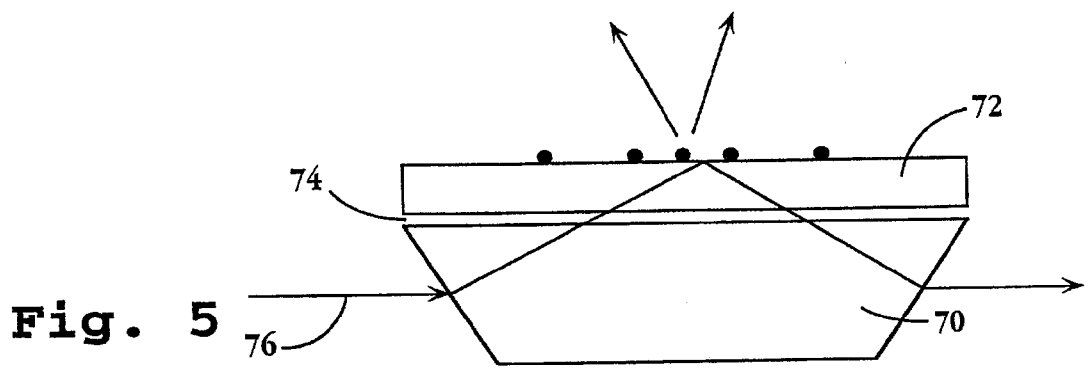
FIG. 5 is an illustration of a total internal reflection type sample stage suitable for use in the observation of plasmon resonant entities.

In another embodiment, illustrated in FIG. 5, a Dove prism 70 is illuminated from the side. A standard glass slide 72 is placed on the top surface of the Dove prism 70, with a suitable index matching oil 74 in between. The incident light 76 is brought in parallel to the major surface of the prism 70 and is refracted up toward the slide 72. The angle of incidence at the slide is selected to be greater than the critical angle, and results in total internal reflection at the upper surface of the slide 72. The light then exits the other side of the Dove prism, again parallel to the major face of the prism 70. Evanescent electromagnetic fields excite PREs bound to the upper surface of the slide, and emit the usual plasmon resonant scattered light into an objective lens located above the slide.

This Dove prism geometry is convenient for bringing light from diverse sources such as laser, quartz halogen, arc lamp and the like via an optical fiber or lens to impinge upon the side of the Dove prism, and filters may be conveniently interposed therebetween to further control the nature of the incident light.

The DARKLIGHT™ light source from Micro-Video of Avon, Mass. can also be used in a total internal reflection illumination system, although it has been found generally inferior to the Dove prism embodiment described with reference to FIG. 5. This totally internally reflecting slide illuminator takes light from a halogen source into an optical fiber, then into the edge of a glass slide. The light undergoes total internal reflection numerous times while spreading down the slide, exciting PREs with evanescent fields as with the embodiment of FIG. 5. This system is described in detail in U.S. Pat. No. 5,249,077. Additionally, PREs can be observed via the illumination described in U.S. Pat. No. 3,856,398.

Oil immersion lens systems can also be used in conjunction with TIR illumination. In these systems, though, the index of refraction of the medium for internal reflection must be greater than that of the oil being used. Accordingly, flintglass, having an index of refraction of 1.7, is one preferred prism material.

Figure 6:
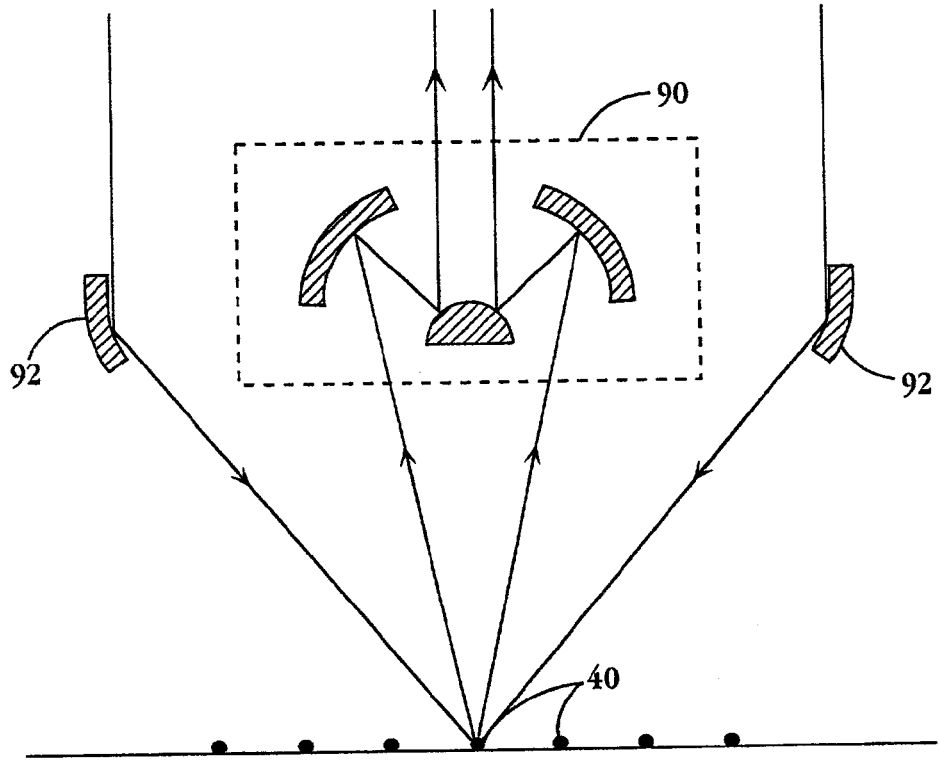
FIG. 6 illustrates a reflecting brightfield/darkfield lens suitable for PRE imaging.

FIG. 6 illustrates in cross section a DF/BF objective lens system comprising a reflective objective lens 90 combined with a suitable enclosing darkfield illumination ring element 92 as an alternative illumination scheme. Although the use of such a two component reflective lens reduces the intensity at the center of the diffraction pattern, the fact that it also substantially reduces the chromatic aberration compared to the refractive lenses described in the prior art, makes it a preferred embodiment in conjunction with the means for obtaining the simultaneous frequency dependent scattering data for a multiplicity of PREs and for the other non-PRE scattering entities within the field of observation that may be imaged and which need to be distinguished and rejected for many applications.

In some applications, optical microscopy methods must be tailored to both optically image and analyze the PREs and also to observe the same PREs and associated sample material with additional instruments such as one or more forms of electron microscopy. In these cases, darkfield optical microscopy must be performed with substrates suitable for electron microscopy as well. Because the electrons must pass through the sample and substrate, the substrate must be very thin, typically well under 1 μm. Common substrates include formvar and/or carbon deposited upon a supporting grid. Background scattering is reduced from the grid boundaries or "bars" by arranging for the field of application of the incident darkfield illumination to be within the spacing of the grid "bars" and/or to restrict the field of view of the collecting objective light for the part of the sample under observation. For the BF/DF objective and microscope system, grids with a spacing of up to 400 bars per inch and silicon nitride membranes are especially suitable. Alternative forms of darkfield illumination include a separate optical fiber or lens with darkfield illumination from below the grid substrate and observation of the scattered PRE light from above with a BF objective lens.

IV. PRP Compositions

The invention further includes a suspension of plasmon resonant particles (PRPs) having one or more populations of PRPs. The composition has four distinguishing features: (i) the PRPs in each population have a spectral width at half-height of less than 100 nm; (ii) the PRPs in a single population are all within 40 nm, preferably 20 nm of a defined spectral emission peak wavelength; (iii) at least 80% of the PRPs in the composition are in one or more of the populations and have a spectral emission wavelength in one of the three ranges >700 nm, 400-700 nm; and <400 nm; and (iv) each population has at most a 30% overlap in number of PRPs with any other population in the composition.

The first feature addresses the quality of the PRPs, high-quality emitters being characterized by a relatively narrow frequency range of scattered light. The second feature provides homogeneity of spectral emission properties for all PRPs within a given population. Specifically, PRPs within a given population all have a peak wavelength within 40 nm of a defined wavelength. The third requirement provides that a large majority of the PRPs (at least 80% by number) are in one of three different wavelength ranges. The fourth requirement defines the uniqueness of the populations, assuming that each population has a distribution of spectral peak wavelengths within 40 nm of a given peak wavelength. The two distribution curves can be no closer than the distance at which 30 number percent of the particles in one population fall within the distribution curve defined by an adjacent population.

Typically, the PRPs in the composition are in one or more of the populations, all in the 400-700 nm wavelength range. The PRPs may be homogeneous, e.g., all blue particles, or may be in one of more populations, e.g., discrete populations of red, green, and blue particles, collectively making up 80% of the PRPs in the composition. Particles in this spectral range may be formed, as described below, as solid silver particles, silver particle with a gold core, or particles with a dielectric core and an outer silver shell of at least about 5 nm.

In one general embodiment, particularly for use in a variety of diagnostic applications, the particles have localized at their surfaces, (i) surface-attached ligands adapted to bind to ligand-binding sites on a target, (ii) fluorescent molecules, and (iii) Raman-active molecular entities. The ligands are one of the members of a conjugate pair that can include antigen/antibody, hormone/receptor, drug/receptor, effector/receptor, enzyme/substrate, lipid/lipid binding agent and complementary nucleic acids strands, as examples.

The PRPs in the composition may have different surface-localized molecules on different groups of PRPs. These different groups may be different PRP populations, that is, PRPs with different spectral peak wavelengths, or may be localized on PRPs in a homogeneous PRP population.

For use in identifying a target having first and second ligand-binding sites, the different surface localized molecules may be different ligands effective to bind to different ligand-binding sites, such as two different-sequence oligonucleotides that bind at different sequence regions of a common target polynucleotide, or two different ligands that bind to different ligand-binding sites on a macromolecular target.

PRPs may be formed made by a variety of known methods, including colloidal chemistry, soluble gel, evaporation/annealing, nucleation/growth via an enhancer, autoradiography, and photoreaction in silver halides and other materials via electromagnetic energy in the form of light, X-rays, or other incident wavelengths. In addition, lithography, electrodeposition, electroplating, and sputtering with a scanning tunneling microscope (STM) tip can be used.

Where the PRPs have surface localized, e.g., attached ligands, the PRPs are able to bind selectively to a target of interest which carries the other half of the ligand/ligand-binding conjugate pair.

As indicated above, it is also advantageous to produce population of PRPs having different defined peak wavelength values. When defined populations of PRPs are combined with specific binding characteristics, a new class of sub-microscopic probe is created which has significant advantages over all currently used labeling techniques. The PRP formation techniques described below may be used to create such probes.

A. Formation of the PRPs by Metal Enhancement

In this method for forming PRPs, a nucleation center, typically a metal nucleation center in the 1-20 nm size range, is placed at a targeted location, followed by in situ development (enhancing) of the full conductive body of the PRP. In some applications, a spatially pre-specified position is designated for the placement of the nucleation center. This is in contrast with other applications where nucleation centers are used to probe a matrix for a particular substance or feature whose position is not known. Pre-specified placement may be advantageous in metrology and/or instrumentation applications which are further described below. For example, it may be desired to place a single PRP on the end of an optical fiber or a scanning microscope tip. Also, it may be desired to create a pattern of PRPs in a particular geometric configuration.

Because it is often desirable to create PRPs with controlled spectral characteristics, the enhancing may advantageously be performed while being monitored, stopping the process when a PRP having some pre-defined spectral characteristic is formed. This is especially convenient when enhancement chemistry which is not affected by light is used. It is also possible to monitor PR formation by periodically terminating the enhancement process, observing the characteristics of the entity or entities formed, and re-initiating the enhancement process if one or more spectral characteristics such as color, for example, are not within a desired range.

The nucleation center is typically a gold particle 1-10 nm in diameter, and the metal used for enhancing this nucleating site to PRP size is silver. However, other elements including, for example, platinum, nickel, and palladium, and macromolecules, such as polynucleotide molecules, are also contemplated as nucleation centers for the subsequent enhancement process. Non-metallic materials may also be used as nucleating centers, such as protein and nucleic acid.

The configuration of the nucleating center can be controlled so as to produce a PRP having a desired shape or characteristic. For instance, triangular or ellipsoidal regions of nucleating material can be formed. The deposition process may involve many metal deposition techniques known in the art, such as vapor deposition, sputtering, Ga-focused ion beam (FIB) milling of the thin film prepared of the desired material, and electroplating into nanopores. Particularly well controlled placement of nucleating material is possible by discharging nucleating material from the metal tip of a scanning tunneling microscope. Techniques have also been developed whereby individual metal atoms are picked up with the tip of a scanning tunneling microscope, moved, and put down at a desired location. Individual atoms may also be "pushed" to a desired location with a scanning tunneling microscope tip. This technique may be used to place, for example, 10 gold atoms at a spatially pre-specified position for use as a nucleation center.

In one embodiment, PRPs or PRP nucleating centers are placed at a desired location by introducing the PRP or PRP nucleating center into a drawn micropipette tip, moving the PRP or PRP nucleating center to a desired location and depositing the PRP at this location using standard micro-manipulation techniques. The pipette tips are filled with the desired material in solutions of varying viscosity (i.e. with gelatin or other matrices), then the tip is manipulated to a selected location while observing under the microscope. By applying pressure to the solution in the pipette, very small quantities can be deposited onto a desired substrate. Other micromanipulation techniques are also possible.

Because the PRP material will have a positive dielectric constant at frequencies above the resonant frequency, the metal particles can be optically trapped in a focused light beam of appropriate wavelength using principles similar to currently practiced optical trapping of plastic particles. The PRP can thus be placed at a spatially pre-specified position by manipulating the light beam in which it is trapped. Channels of gel may also be created in order to route PRPs to spatially pre-specified positions electrophoretically. If the channel is configured to pass proximate to a designated location, a PRP in the channel will move under the influence of an electric field so as to be guided to the location. Electrostatic bonding techniques can also be used to removably attach PRPs to spatially pre-specified positions.

In one embodiment, an array of one or more conductive pads of approximately 10 to 100 microns in diameter may be created using standard integrated circuit lithographic techniques. Each pad may further be selectively connected to a voltage source. As PRPs in solution can be negatively charged, applying a suitable potential to a pad will attract a PRP from solution and onto the conductive pad. Removing the voltage and reversing the sign of the applied potential may free the PRP if the surface binding forces between the PRP and the pad are weak, i.e., approximately one picoNewton.

Conjugated nucleating centers and/or conjugated PRPs can also be placed at a spatially pre-specified position by immobilizing the other half of the conjugate pair at the spatially pre-specified position and binding the conjugate on the nucleating center or PRP to the other half of the conjugate pair.

Individual nucleating centers (or fully formed PRPs) may also be deposited by ejecting droplets of metal particle containing fluid to a substrate and having the fluid evaporate away by techniques analogous to those used in ink jet printing. In this technique, one or more metal particles can be delivered to a specific location defined by the drop position. In some embodiments, the concentration of PRPs or nucleating centers in the fluid is chosen so that it is statistically likely for one or no PRP or nucleating center to be contained in each drop. If nucleation centers are deposited, they may be subsequently silver enhanced to form PRPs. It may further be noted that these techniques can be used to create a desired geometric pattern of PRPs. When making such a pattern, drops can be redeposited at those locations where no PRP was ejected during the first pass. Articles with such patterns of PRPs can be useful in object identification, semiconductor mask registration, and other uses as are described in more detail below.

As defined herein, the term "in situ" indicates that the PRP is bound to a substrate, immersed in a solution or suspended in a matrix. The definition of "substrate" is discussed below and includes any entity with which a PRP can associate such as tissue sections, cells, TEM grids made from, for example, formvar, silicon (including silicon nitride and silicon dioxide), mica, polystyrene, and the like. These nucleation centers are typically colloidal gold preparations, and suitable populations of nucleation centers are commercially available either in free form or attached to various biological molecules.

The silver enhancement of gold nucleating centers to produce larger silver masses which can be visible under an electron and/or a light microscope is currently practiced, and some procedures for imaging biological systems using silver enhanced gold particles have been extensively developed. Reagents for performing the enhancement, as well as the nucleating centers themselves, are accordingly commercially available. Antibody bound gold nucleation centers are available from several sources, including E-Y Laboratories of San Mateo, Calif., and Amersham of Arlington Heights, Ill. Furthermore, a large body of literature describes a variety of suitable methods for performing such enhancement (see, for example, M. A. Hayat, Ed., Immunogold-Silver Staining—Principles, Methods, and Applications, CRC Press, 1995, the disclosure of which is hereby incorporated by reference in its entirety, most particularly Chapters 2 and 7, which describe several experimental techniques for silver enhancing gold nucleation centers and a discussion of the silver masses formed thereby).

The enhancement process is preferably performed by mixing gold nucleation centers with a solution of a silver salt such as silver acetate, silver lactate, or silver nitrate, and a reducing agent such as hydroquinone in a citrate buffer at a pH of approximately 3.5 to 3.8. It has been suitable to provide a concentration of approximately 6 mM for the silver salt and approximately 33 mM for the hydroquinone. Commercially available silver enhancement solutions containing appropriate quantities of silver and reducing agents are also commercially available from, for example, BBI of the United Kingdom. Those of skill in the art will appreciate that choice of buffering system, silver salt, reducing agent, and other enhancement parameters are preferably optimized for the local environment, target locations, and the like, and that such optimization can be performed without undue experimentation.

In accordance with one aspect of the present invention, PRPs useful in the invention are prepared by silver enhancing nucleating centers until the particles possess the properties of plasmon resonant particles. Most preferably, the silver enhancement parameters are controlled such that the PRPs created have pre-defined spectral characteristics, such as appearing a particular desired color when viewed with darkfield microscopy. During enhancement, spectral characteristics may be observed for one individual evolving PRP or simultaneously for a plurality of individual PRPs. Thus, PRPs having specific physical properties can be made and placed at a desired location. In addition, PRP nucleating centers can be placed at a desired location, either in situ, in vitro or in vivo, followed by silver enhancement to produce a PRP at the specific location.

B. Specific Examples of PRP (or PRE) Formation by Metal Enhancement

PRPs were prepared by silver enhancement of a gold nucleating center as described in the following examples.

EXAMPLE 1

Placement of Gold Colloids on a Substrate

The Alcian Blue method is one method for attaching gold colloid nucleating centers to a substrate by chemically treating one or more spatially pre-specified positions of the substrate. Alcian blue is a positively charged dye which promotes adhesion of the negatively charged gold colloids by charge interactions. Portions of the substrate at which PRPs are undesired may be coated with a blocking agent such as BSA. A 100 microliter drop of 100:1 dilution of 5% acetic acid and 2% alcian blue was placed onto a carefully cleaned glass slide for ten minutes. The active site of the substrate was then immersed in doubly distilled water, rinsed, and dried.

The gold colloids were diluted to the desired concentration. The solution was placed on the alcian blue treated region of the substrate and incubated for 10 minutes. The substrate was then rinsed with distilled water.

The gold colloid attached to the substrate was enhanced as described in Example 2.

EXAMPLE 2

Silver Enhancement of Individual Gold Nucleating Centers

One ml of a 0.1 mg/ml solution of gelatin was mixed with 50 µl initiator and 50 µl enhancer in an eppendorf tube. The initiator and enhancer were obtained from BBI International (United Kingdom) silver enhancement kit, light microscopy (LM) version, catalog No. SEKL15. The substrate was immediately covered with the enhancer solution and timing was started. The substrate was then viewed under darkfield illumination to determine whether PRs were present. The approximate enhancement time for colloids on glass, silicon or TEM substrates was about one minute, while the approximate enhancement time for conjugate colloids attached to biological substrates was about seven minutes. These times were determined by continuously observing the scattered light from an individual evolving PRP under darkfield microscopy while the enhancement was taking place. It can be appreciated that precise enhancement durations can be utilized to control the scattering response, and therefore the color, of the PRPs created. Enhancement was stopped by rinsing thoroughly with distilled water.

EXAMPLE 3

Generation of PRPs in Solution

For uncoated colloids, 100 μl stock gold colloid (BBI International, United Kingdom) was added to 20 ml gelatin solution (0.1 mg/ml). For protein conjugated colloid, 100 μl stock conjugated gold colloid was added to 20 ml doubly distilled water with 1% bovine-serum-albumin (BSA) to block the surface. Conjugated colloids used were bovine serum albumin, goat anti-biotin and rabbit anti-goat IgG. Typical gold colloid concentrations are:

For uncoated colloid:
3 nm stock—~$3\times10^{13}$ particles/ml
10 nm stock—~$5.7\times10^{12}$ particles/ml
20 nm stock—~$7\times10^{11}$ particles/ml For protein conjugated colloid:
1 nm stock—~$2\times10^{15}$ particles/ml
5 nm stock—~$1.7\times10^{14}$ particles/ml
10 nm stock—~$1.7\times10^{13}$ particles/ml
20 nm stock—~$2\times10^{12}$ particles/ml Three drops (150 μl) initiator was then added. Ten μl increments of enhancer were then added while stirring, until the amount corresponding to the desired PRP scattering peak wavelength was added. The PRP resonance was checked by darkfield measurement or by absorption spectroscopy as described previously.

C. PRP and PRE Formation with Lithography and Illumination

Lithographic techniques can be used to specify where a PRP (or PRE) will be formed and to control its shape, shape, morphology and composition. Both positive and negative resist methods can be utilized to lay down either nucleation centers or fully formed PRPs. In the positive resist method, portions of a layer of resist is removed in order to form molds into which metal is deposited. After such deposition, resist and extra metal is lifted off, leaving a nucleating center or a fully formed PRP behind. In the negative resist method, a chosen layer of silver or other suitable metal is covered with a layer of resist. Portions of this resist layer are then polymerized. When nucleation centers are formed with this technique, the characteristic size of this polymerized region may advantageously be approximately 5-20 nm. For laying down PRPs whose peak wavelengths are in the optical spectrum, the characteristic sizes of the polymerized regions are advantageously 40-125 nm. Silver and unpolymerized resist are then etched away, leaving the metal nucleation centers or fully formed PRPs under the polymerized portions of the resist. As another alternative, metal forms can be produced which are larger than desired, and material may be etched away by ion milling until a PRP of desired characteristics is formed. All of these techniques are used in the electronics and other industries and are well understood by those of skill in the art.

In addition, metal salts and halides (i.e. in film) can be irradiated to obtain nucleation centers or entire particles. Enhancement can be performed with the techniques set forth above, or can also be performed by thermally annealing the metal particles, or may be performed as is done in photographic development processes, wherein a film of photochemical metal salts or metal halides is locally irradiated with light until PRPs are produced, and the film is then fixed and developed. There are several ways a localized light spot may be produced for forming nucleating centers or PRPs at desired locations. In one embodiment, a very localized light spot can be generated using a metal side-coated tapered fiber "near-field" scanning tip to help confine the nucleation to a suitable small size or to grow the silver grains directly. Alternatively, a pre-made special optical fiber tip of preferably approximately 150 nm diameter having a PRP on its end concentrates the light at a desired location to "write" these nucleation centers onto a photosensitive surface material. In another embodiment, a solid-immersion lens may be utilized to focus the light onto the metal salts or halides. The solid-immersion lens may include a PRP at its focal point in order to further intensify the local radiation of the substrate.

Photochemical silver salts or halides are also sensitive to electron and ion beam irradiation, as well as irradiation from radioactive elements. It will be appreciated that these photographic methods can also be used to produce arrays or patterns of PRPs of desired configuration.

Whether the developing PRPs are in solution, or bound to a substrate, the enhancing process can be observed in situ with darkfield microscopy and the process stopped once the PRP has reached the desired size which corresponds to a particular color. During light sensitive enhancement procedures, the progress of the enhancing process can be observed by washing out the enhancer, observing the light scattering properties of the particles created, and re-initiating enhancement until PRPs with desired spectral characteristics are obtained. In an alternative embodiment, a relatively light insensitive enhancer can be used and the enhancing process can be observed under continuous darkfield illumination and scattering data collection. Of course, once specific protocols have been developed which indicate enhancer amounts, incubation times, etc., to produce PRPs with given properties, observation of the enhancement process becomes unnecessary.

D. Formation of a Conjugated PRPs

As is shown in Example 3 above, it is possible to enhance nucleating centers which are bound to a biological macromolecule such as an antibody. This enhancement of conjugated gold antibodies can be successfully performed even when the conjugated gold/antibody is in aqueous solution and has not been previously bound to an antigen in a cell or cell organelle. Surprisingly, it has been found that after silver enhancement of free conjugated gold nucleating centers to create PRPs, an appreciable fraction of the conjugate molecules originally present on the gold colloid are surface bound to the resulting PRPs. Furthermore, the biological molecule can retain biological activity after the enhancement process.

In conjunction with this method, the amount of bound conjugate on a given PRP can be controlled by controlling the size of the conjugate bound nucleation center. For example, a commercially available 1 nm diameter nucleation center may have only one conjugate molecule, and be silver enhanced to form a PRP with that conjugate molecule attached on the outermost surface thereof. A 20 nm nucleation center will have a correspondingly larger number of conjugates attached, some of which will end up bound to the surface of the silver enhanced PRP. During silver enhancement, the conjugate bound PRPs can be incubated with a blocking agent such as bovine serum albumin (BSA) to reduce the presence of non-specific bonding sites on the surface of the PRP.

In another embodiment, a conjugate is added to a PRP after the PRP is made. The conjugate associates with the PRP either covalently or noncovalently. For example, a fully formed PRP is coated with gelatin, agar, polytetrafluoroethylene (Teflon®), PVP, or latex to prevent non-specific charge interactions, followed by covalent attachment of one or more functional groups thereto by well known methods, thus generating a PRP attached to a first half of a particular conjugate pair. The reagents required to couple conjugates to immunogold nucleating centers or formed PRPs are all commercially available.

This method of forming conjugate bound PRPs also allows control of the number of conjugate molecules (i.e. "first half" conjugate pairs) bound to the surface of the PRE. In this case, one can incubate bare PRPs in a solution of conjugate and a blocking agent such as BSA. The relative concentrations of conjugate and BSA can be adjusted to produce, on average, the desired amount of conjugate on each PRP. For PRPs of unusual shape, or comprising concentric shells of different materials, coating with conjugates after formation is typically more convenient. Conjugate bound PRPs which are approximately spherical, however, can conveniently be produced from commercially available conjugate bound gold colloid nucleating centers and silver enhancers as described above.

Conjugates or other molecules may be bound directly to the metal surface of the PRP. The surface chemistry involved in such binding is complex, but it is currently exploited extensively in many non-PRP immuno-gold silver staining techniques. Alternatively, the PRPs may be coated with a shell of plastic material such as latex prior to the binding of additional molecules such as conjugate. Techniques for binding molecules to latex are also well known. The molecules bound to the metal directly or plastic shell may be the conjugate itself, or may be other intermediate reactive groups such as sulfides, amides, phosphates, aldehydes, carboxyl, alcohol, or others to which conjugate or other molecules of interest may be bound. Conjugates or other molecules of interest may be synthesized onto such a reactive base with known techniques of combinatorial chemistry.

E. Formation of PRP Populations with Desired Characteristics

The differences in emission spectra for the two separate PRPs as shown in FIG. 1 can arise from a number of factors. One significant factor is size, particles of larger size having resonance peaks at longer wavelengths, and also having spectral shapes with increased half-maximum widths. Therefore, control of the size of PRPs being produced results in control over some spectral characteristics.

It can thus be appreciated that with the addition of a controlled amount of enhancer, a population of PRPs with a narrow range of diameters, and therefore a correspondingly narrow range of resonant peak frequencies, may be produced, such as is illustrated in FIG. 2 for four types of PRPs. In some advantageous PRP production methods, the particles can be observed during the enhancement process with a suitable microscope. These methods use enhancement chemicals such as are described herein which are relatively unaffected by incident light needed to observe development of the PRP during the enhancement process. Thus, PRP development can be observed and halted when it has reached a desired endpoint. For those applications in which it may be desirable to use a light sensitive enhancement process, or if development outside the microscope is desired, timed sequential enhancement is performed. The samples are rinsed after each application and the status of PRP light scattering is determined. One can continue with as many sequential enhancement steps as desired.

As indicated above, the PRP composition of the invention includes one of more PRP populations having peak wavelengths 40 nm of a defined wavelength. Such homogeneity in PRP population is possible by stepwise addition of enhancer coupled with darkfield observation of the PRP creation as described above. Because the width of a plasmon resonance peak is typically 20 to 40 nm, it is generally unnecessary to further reduce the variance in resonance peaks of the PRP population.

Populations of PRPs having uniform spectral characteristics can alternatively also be prepared by purifying non-homogeneous populations. PRP conjugates and free PRPs can be separated by conventional biochemical methods including column chromatography, centrifugation, electrophoresis and filtration. Because PRPs with surface localized molecules or entities can have a significantly different mobility than do free PRPs of the same size, they elute from gel filtration columns at a different rate than do free PRPs. Because PRPs are charged particles, they migrate in an electric field. Thus, PRPs can be manipulated by and even observed during electrophoresis.

PRPs having certain desired characteristics can also be separated based on their Zeta potentials. Zeta potential separation equipment suitable for this use is commercially available (Coulter Corp, Florida). Radiation pressure may also be used to force PRPs through a matrix at different rates depending on their structural properties. If bound and free PRPs are subjected to electrophoresis in, for example, an agarose or acrylamide gel, the free PRPs migrate faster than do the bound PRPs. Likewise, PRP conjugates may be preferentially retained by filters. Purification can alternatively be performed by centrifugation. Thus, with these methods, an original population of PRPs having a wide range of spectral characteristics can be separated into subpopulations which have a narrower range of spectral characteristics.

Individual populations of PRPs, may be prepared separately and later mixed according to a desired combination of PRP property, e.g., color, in desired amounts, each labeled with the same or different biological macromolecules or unlabeled depending on the application. In such compositions, it is preferable for the resonance peaks of the different populations of PRPs to be substantially non-overlapping, as defined above. In some preferred embodiments, the variance in peak location of one population of PRPs is controlled to be within approximately 20 nm of one defined wavelength, and the variance in peak location of another population of PRPs in the mixture is controlled to be within approximately 20 nm of a second defined wavelength. To avoid significant overlap, it is preferable to ensure that the two peak wavelengths are at least 30 to 40 nm apart, and most preferably 50 or more nanometers apart.

Applying the above methods, new types of molecular probes can be produced by binding selected conjugates to selected PRPs. As mentioned above, a PRP population with a first spectral characteristic can be bound to a first conjugate, and a PRP population with a second spectral characteristic can be bound to a second, different conjugate to produce two differentiable populations of PRPs with different preferential binding properties. Such pre-defined mixtures of PRPs are especially useful in improving the accuracy of detection of low abundance molecules as will be explained further below.

F. Isolated Non-Spherical and Composite PRPs

The emission spectra of PRPs is further affected by the details of their structure. Ellipsoidal PRPs offer additional parameters for identification and discrimination. Each ellipsoidal PRP may have two or three plasmon resonant peaks, depending on whether there is one isotropy axis or three different principal axis dimensions, respectively. Ellipsoidal PRPs having one isotropy axis show peaks corresponding to two orthogonally polarized emissions, one associated with plasmon excitation along the major axis of the ellipse, the other associated with plasmon excitation along the minor axis. The distinct plasmon resonance peaks occur at maximal intensity when the polarization of incident light is along the corresponding principle axis. Thus, the response of a fixed ellipsoidal PRP to polarized light may vary with the direction of incidence.

A process for making ellipsoidal silver particles consists of pulling on a glass matrix containing spherical PRPs at a temperature such that the viscosity results in a stretching of the PRPs into prolate ellipsoidal particles having a desired aspect ratio. Conditions have also been described for "pushing" on such particles such that they form oblate ellipsoidal particles. One ellipsoidal PRP containing matrix, Polarcor® (Corning Company, Corning, N.Y.), consists of aligned ellipsoidal PRPs in a glass matrix. This composite material is an effective polarizes for certain optical frequencies, principally in the red and above. Individual ellipsoidal PRPs contained within such a glass matrix can be isolated by dissolving the matrix in such a manner so as to not disturb the PRPs. By preparing ellipsoidal gold particles of the correct aspect ratio and size in a suitable matrix, then dissolving the matrix in a manner that does not disturb the particles, large quantities of ellipsoidal of PRPs having approximately equivalent plasmon resonance scattering properties can be prepared for use in, for example, liquid reagent preparations for biochemical assays as described in detail below.

Other methods can be used to prepare ellipsoidal PRPs, which may be produced via photoreaction of silver halides or with appropriate lithographic molds. Alternatively, PRPs which are originally formed to be substantially spherical can be pressed or rolled between two surfaces to flatten them into a desired oblate or prolate ellipsoidal configuration.

Non-spherical and non-ellipsoidal PRPs are observed to have characteristic spectral signatures which are different than spherical and elliptical particles, and which are useful in creating plasmon resonant probes with advantageous size and scattering properties. It has been found that PRPs which scatter strongly in the blue region may be conveniently produced by making spherical silver particles. As discussed above, increases in particle diameter will red shift the resonant peak. However, for spherical particles, the peak intensity of the scattered light begins to drop off as the peak is shifted into the red, and accordingly strong red scatterers are much more difficult to produce with spherical particles than are strong blue scatterers. Particles of other geometric shape, however, can produce strong scattering at longer wavelengths. Three such particles are triangular, square, and approximately hexagonal in cross-section. Triangular, square, and hexagonal silver particles may, for example, be produced via photoreaction of silver halides or with appropriate lithographic molds. Isolated hexagonal particles of a similar size as a blue spherical particle will typically have a green plasmon resonance peak. The isolated triangular particles, which may have 50-150 nm characteristic dimension, are of particular interest because they often exhibit a resonance peak in the red part of the visible spectrum. It has been found that production of triangular PRPs is one suitable method of obtaining PRPs which appear red. A specific example of a red triangular particle and a blue spherical particle are discussed below with reference to FIGS. 7 and 8. It is also possible to bind small spherical metal particles into pairs or other conglomerates to form a variety of plasmon resonant particle shapes.

In addition, PRPs having concentric shells of dielectric and conductive material can be prepared. In these embodiments of PRPs, the peak of the plasmon resonance can be tuned to a desired frequency. Specifically, PRPs can be made with the addition of dielectric material as either the core or external shell tends to red shift the resonant peak and produces a comparably strong scatterer. For this reason, red PRPs may advantageously be produced with the inclusion of such a dielectric shell or core. Particles having a dielectric core and a shell of aluminum have been found to have a plasmon resonance peak in the ultra-violet, at approximately 240-280 nm.

Particles of three layers comprising a dielectric core/metal shell/outside dielectric shell may be useful for further flexibility in changing the peak response and the scattering strength. In addition, a PRP with multiple concentric conductive shells can be created. Because each shell will have a different diameter, complex scattering spectra often containing several separate peaks can be produced. These peaks can be shifted with variations in the dielectric material separating the conductive shells. As will be explained in more detail below, a dielectric outer shell, comprising latex, teflon, or other polymer coating, is also useful as a substrate suitable for binding macromolecules of interest to the outside of the PRP.

The production of PRPs having multiple shells of conductive material and dielectric can be more complex, but these may be manufactured with various film deposition techniques including chemical vapor deposition or sputtering. Other methods for fabricating multi-shelled PRP embodiments are described in U.S. Pat. No. 5,023,139 to Birnboim et al., mentioned above.

A PRP having a dielectric core and an outer metal shell can also be made with electroless plating techniques. In this process, core particles, made, for example, from latex, have their surfaces activated with metal atoms which may be platinum atoms. Using enhancement procedures as described above, these platinum atoms comprise nucleation centers for silver enhancement and the formation of a shell around the latex core.

PRP compositions which may, but do not necessarily include all of the limitations (i)-(iv) in the PRP composition just described are also contemplated herein, as novel PRP compositions for use in a variety of applications discussed herein, including the general method disclosed in Section III.

Two-ligand composition. The composition contains two populations of PRPs, each having a different ligand species carried on the PRP surface. The two ligands are designed to bind to different ligand-binding sites on a target. The two populations PRPs may have different spectral properties.

Fluorescent-reporter composition. The composition includes PRPs having surface attached ligands, for binding to the ligand-binding sites of a target. The composition is a very sensitive, "one-site" reporter, in that fluorescence emission excited by the plasmon resonance spectral emission of the associated particle acts to focus excitation light at the site of the fluorescent molecules. The composition may also be sensitive to the target environment, if such is designed to contain fluorescence quenching or fluorescence energy transfer molecules.

Fluorescent Quenching or Energy Transfer. This composition includes two populations of PRPs, each having a surface-attached ligand (which may be the same or different) for binding to two proximate sites of a target. Each population contains surface-localized florescent molecules which either produce fluorescence quenching when proximately disposed, or which contain donor and acceptor fluorescent molecules for non-radiative energy transfer when proximately disposed. The composition is useful, for example, in a homogeneous assay for detecting a target with first and second proximate ligand binding sites.

PRPs with Raman-active entities. The composition includes a plurality of PRP populations, each with a different Raman-active entity localized on the PRP surfaces. Each population may contain additional surface-localized molecules, e.g., oligonucleotides with different base sequences or combinatorial library molecules, where the identity of each surface-localized molecule is associated with a Raman-active entity, e.g., molecule, with a known, unique Raman spectrum signature. The composition is used, for example, to identify combinatorial library compounds that are (i) formed on the PRPs according to standard bead-synthesis methods, and (ii) identified as having a desired compound activity.

As another example, the composition is used for chromosome mapping, where the relative spatial positions of known sequence regions, e.g., ESTs or SSTs, are determined by (i) attaching to each PRP with a unique Raman spectral signature, an oligo sequence fragment complementary to one of the chromosome sequences, (ii) hybridizing the probes with the chromosomal DNA, and (iii) identifying from the unique spectral signature of each PRP, the relative position of the PRPs bound to the DNA. By placing the DNA in an extended condition, as above, the mapping distances separating the sequences can also be determined.

Figure 13:
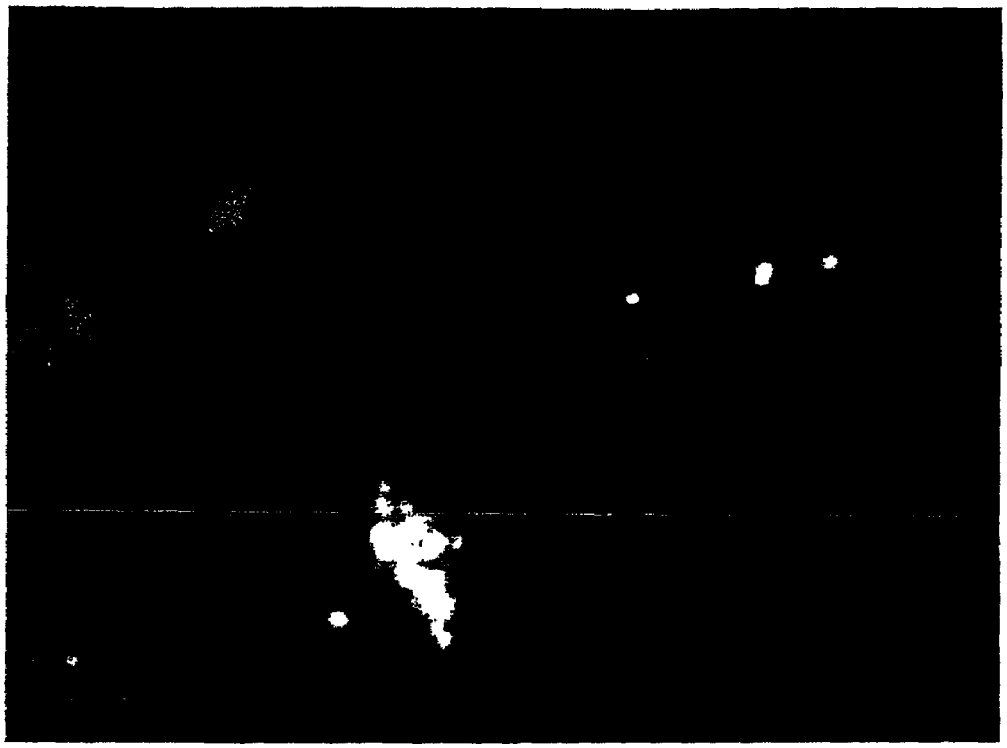
FIG. 13 is a Drosophila polytene chromosomes where a specific gene has been labeled by PRPs.

FIG. 13 shows the binding of an DNA-sequence labeled PRE to a Drosophila polytene chromosomes, illustrating the ability to localize PREs in a chromosome region.

V. Diagnostic Methods and Compositions

The diagnostic method of the invention is intended for use in determining the presence of, or information about, a target having a molecular feature of interest. The method is preferably practiced in accordance with the method and apparatus described in Section III, and preferably employing the PRPs described in Section IV, where the PRPs have surface localized ligands.

In practicing the method, the target is contacted with one or more PREs having surface localized molecules, to produce an interaction between the molecular feature and the localized molecules. This interaction may include (A) binding of a PRE to a target binding site, for example, through a ligand/ligand-binding interaction, to produce a PRE/target complex, (B) binding of two PRPs to closely spaced target sites, to produce a spectral characteristic evidencing a PRE/PRE interaction, (C) cleavage of a linkage between two PREs, to produce unlinked PREs, (D) binding of a PRE to a target, e.g., through a ligand/ligand-binding interaction, to alter the Raman spectrum of Raman-active molecules on PRE in a detectable fashion, (E) binding of a PRE to a target, e.g., through a ligand/ligand-binding interaction, to alter, e.g., quench or enhance the intensity of the fluorescence emission of fluorescence molecules on a PRE in a detectable fashion, and (F) formation of a linkage between PREs to produce coupled PREs.

The target is illuminated with an optical light source, in a manner which allows one or more selected plasmon resonance spectral emission characteristics to be determined, as detailed in Section III. The presence of or information about the target by is then determined by detecting a plasmon resonance spectral emission characteristic of one or more PREs after such interaction with the target.

The PREs employed in the method are preferably PRPs constructed as above to contain a surface-localized molecule that is one of a ligand/ligand-binding site conjugate pair, such as antigen/antibody, hormone/receptor, drug/receptor, effector/receptor, enzyme/substrate, lipid/lipid binding agent and complementary nucleic acids strands. Where the spectral emission characteristic detected is related to a shift or change in Raman or fluorescence spectral characteristic, the PRPs also contain surface-localized fluorescent or Raman-active molecules of entities, respectively. The PRPs employed may have the quality and homogeneity attributes of the PRP composition disclosed in Section IV, or may have less stringent uniformity attributes.

Because PRE probes are extremely sensitive (as noted above, one can observe and spectrally analyze a single PRE), the method may be made very sensitive to amount of target analyte (down to one event). This allows earlier detection of pathogens in bodily fluids, including earlier detection of HIV, tumor markers and bacterial pathogens, detection from smaller fluid volumes, and the ability to miniaturize many existing diagnostic tests.

A. Binding of a PRE to a Target Binding Site

In this general embodiment, PREs with surface ligand molecules are contacted with a target under conditions that lead to PRP-bound ligand binding to ligand-binding sites on the target, forming one or more PRE/target complexes with the target. Typically, the spectral emission characteristic(s) being measured are unchanged by complex formation. That is, neither PRP/PRP proximity spectral emission effects or changes in spectral emission characteristics caused by PRP interactions with the target are observed.

Typically in this embodiment, the target being analyzed is immobilized or competes for an immobilized binding site. After PRP binding to the solid phase, immobilized surface, the solid phase is washed to remove non-bound PRPs before illuminating the target and detecting a plasmon resonance spectral characteristic of the target complex(es). The PREs contacted with the target may include two or more populations, each with different ligands, and preferably each with different spectral signatures associated with different ligands, e.g., blue particles for one ligand, and red particles for another. As will be detailed below, this embodiment has applications for:

(i) detecting the presence of an target analyte, where the analyte is either immobilized, competes with an immobilized binding agent, or can be separated from unbound PRPs in the contacting mixture;

(ii) in situ hybridization of PRP-oligonucleotide conjugates with a DNA target, to isolate PRPs at the site of sequence hybridization;

(iii) mapping spatial features of the target, for example, the arrangement of a specific binding site on a target cell or tissue, or in a DNA target, for chromosome mapping; and (iv) In situ labeling of a target, for example, in a Southern blot, directly binding probe-labeled PRPs to a DNA fractionation gel, to identify separated DNA bands.

The following examples illustrate various assays in which PRPs with surface attached ligand molecules are bound to immobilized target tissue, for purposes of detecting spatial features of the binding sites, and/or the density of binding sites.

EXAMPLE 4

Labeling of Ryanodine Receptor in Chicken Muscle with PREs

Figure 12:
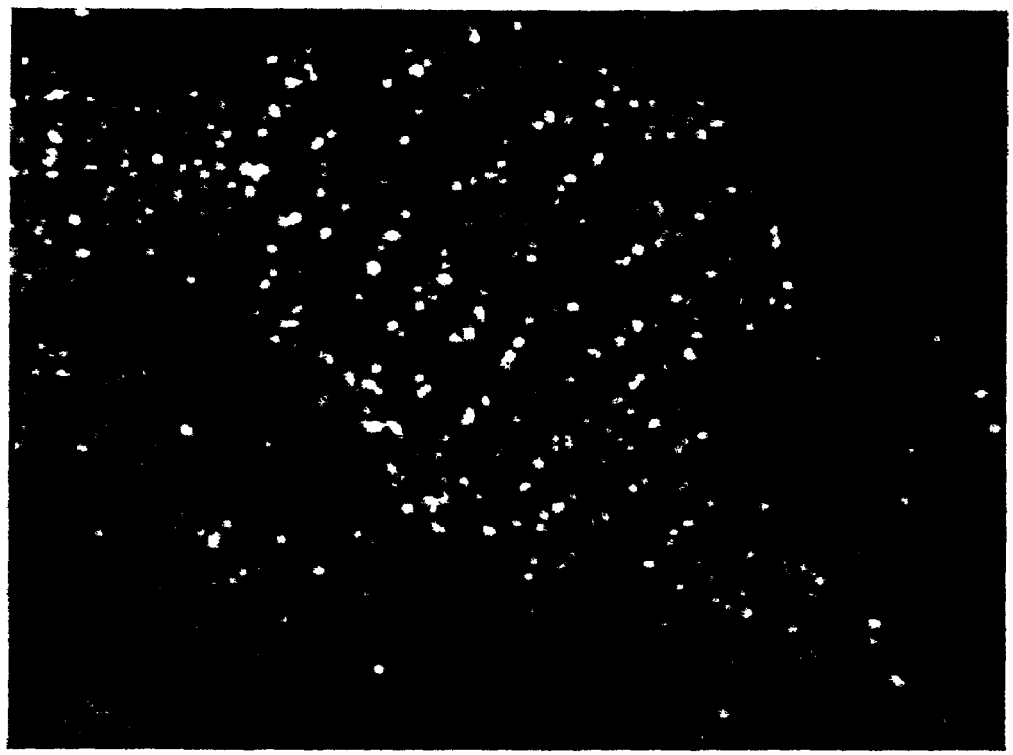
FIG. 12 is a chicken skeletal muscle section whose ryanodine receptors have been labeled with anti-ryanodine PRPs.

Frozen chick intercostal muscle fixed in paraformaldehyde was cut in 2-3 µm sections and transferred to prepared coverslips (Cell Tak coated spots in Pap pen wells). Tissue sections were washed three times for 5-10 minutes each time with PBS. Nonspecific binding sites were blocked by incubation in 3% normal goat serum, 1% gelatin, 0.01% Triton X-100 in PBS for 20 min. Coverslips were washed for 5 min with a 1:3 dilution of blocking buffer (working buffer), then incubated in a 1:5 dilution of mouse anti-ryanodine monoclonal antibody (34C) in working buffer for one hour. Coverslips were then washed 6 times for 3-5 minutes each time with working buffer, followed by incubation with a 1:40 dilution of 5 or 10 nm gold particles conjugated to goat anti-mouse IgG (AuroProbe EM, Amersham) for 30 minutes. Coverslips were washed 3 times for 3-5 minutes each with working buffer, then 3 times for 3-5 min with PBS. Samples were washed 3 times for 2 min in doubly distilled water, then silver enhanced for 8 min using 50 µl initiator, 50 µl enhancer (IntenSE M Silver Enhancement kit, Amersham) and 1 ml 0.1 mg/ml gelatin. Samples were washed three times for 3-5 min with doubly distilled water, covered with Gelvatol anti-fade media and visualized under darkfield microscopy. Individual PREs were observed regularly spaced along the Z-lines of the muscle which contain the ryanodine receptors. The results are shown in FIG. 12.

EXAMPLE 5

Binding of PREs to DNA on Nitrocellulose

A 1 cm×3 cm piece of nitrocellulose membrane was cut and the top surface was marked at one end with a pencil to identify the DNA surface. Biotinylated DNA (100 ng) was pipetted onto one end of the surface of the marked nitrocellulose. Non-biotinylated DNA (100 ng) DNA was applied to the other end as a control. The nitrocellulose was placed in a desiccator to dry the DNA spots, then cross-linked with ultraviolet light. The nitrocellulose, DNA surface up, was placed in a small parafilm dish and incubated for at least 4 hours in blocking solution (50 mM sodium phosphate, 150 mM NaCl, 2% BSA, 1% Tween-20) at room temperature in a 100% humidity chamber to prevent evaporation. A goat anti-biotin immunogold conjugate (Nanoprobes, Inc., Stony Brook, N.Y.; about $1 \times 10^8$ colloids), was added and the incubation continued for 2 hours at room temperature. Immunogold conjugates were removed, blocking solution (500 µl) was added, and the nitrocellulose was washed for one hour at room temperature. Blocking solution was removed and the filter thoroughly rinsed with doubly distilled water. Double distilled water (2 ml) was added to the filter which was washed for 30 min. After removal of the water, one ml enhancer solution (1 ml 0.1 mg/ml gelatin, 50 µl initiator, 50 µl enhancer; enhancer and initiator were from BBI International, United Kingdom, Ted Pella Catalog #SEKL15) was placed on the nitrocellulose for 8 minutes. The enhancer solution was then washed away thoroughly with distilled water. The nitrocellulose was placed on filter paper, DNA side up, in a desiccator to dry for one hour, then placed on a glass slide, DNA side up, and covered with a glass coverslip. The slide was placed in an acetone fume chamber for 20 minutes or until the nitrocellulose became transparent. PREs were viewed using a darkfield microscope. A high density of PREs were observed where biotinylated DNA was spotted compared to a low density of PREs elsewhere on the nitrocellulose, including where non-biotinylated DNA was spotted. The same experiment also successfully detected biotinylated DNA when fully formed PREs conjugated to goat anti-biotin were used.

EXAMPLE 6

Binding of PREs to DNA in Polystyrene Cell Culture Dish

Doubly distilled water (150 µl) and 1 M NaHCO.sub.3 (17 µl) were added to one row of wells in a 48 well culture dish. Neutravidin (10 µg) was added to each dish followed by incubation overnight. All incubations were performed at 4° C., 100% relative humidity. Neutravidin was removed and the wells were thoroughly rinsed with doubly distilled water. 150 µl of blocking buffer (50 mM sodium phosphate, 150 mM NaCl, 2% BSA, 1% Tween-20) was added to each well followed by a 4 hour incubation. Beginning with the second well, 1 µg biotinylated DNA was added to the blocking buffer. In subsequent wells, 10-fold dilutions of biotinylated DNA were added (0.1 µg, 0.01 µg, . . . ) and the plate was incubated for 4 hours. Biotinylated DNA was removed and the wells were thoroughly rinsed with doubly distilled water. Blocking buffer (150 µl of the buffer described above) and approximately $10^8$ goat anti-biotin conjugated immunogold colloids was added to each well and incubated for 4 hours. The immunogold colloid was then removed, wells were thoroughly rinsed with doubly distilled water, and colloids were enhanced by applying 100 µl enhancer solution to each well for 7 minutes. Enhancer solution was removed, wells were thoroughly rinsed with doubly distilled water and wells were dried with dust-free compressed air. PRE concentration in each well was determined using darkfield microscopy. The PRE concentration was correlated with the DNA concentration in each well. The same experiment also successfully detected biotinylated DNA when fully formed PREs conjugated to goat anti-biotin were used.

Figure 7:
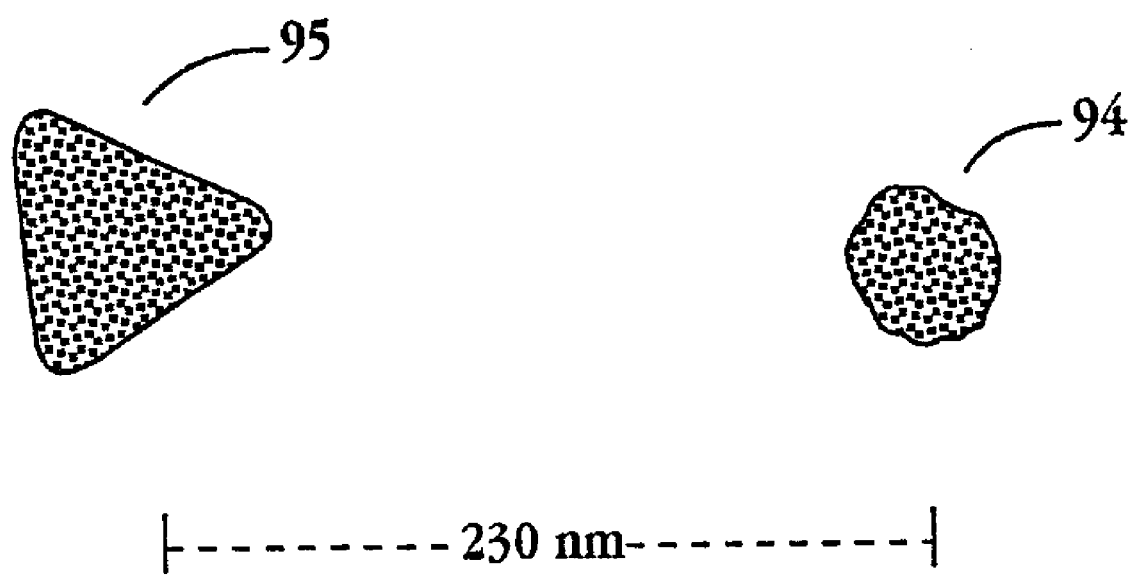
FIG. 7 is a reproduction of a transmission electron microscope image of two plasmon resonant particles.
Figure 8:
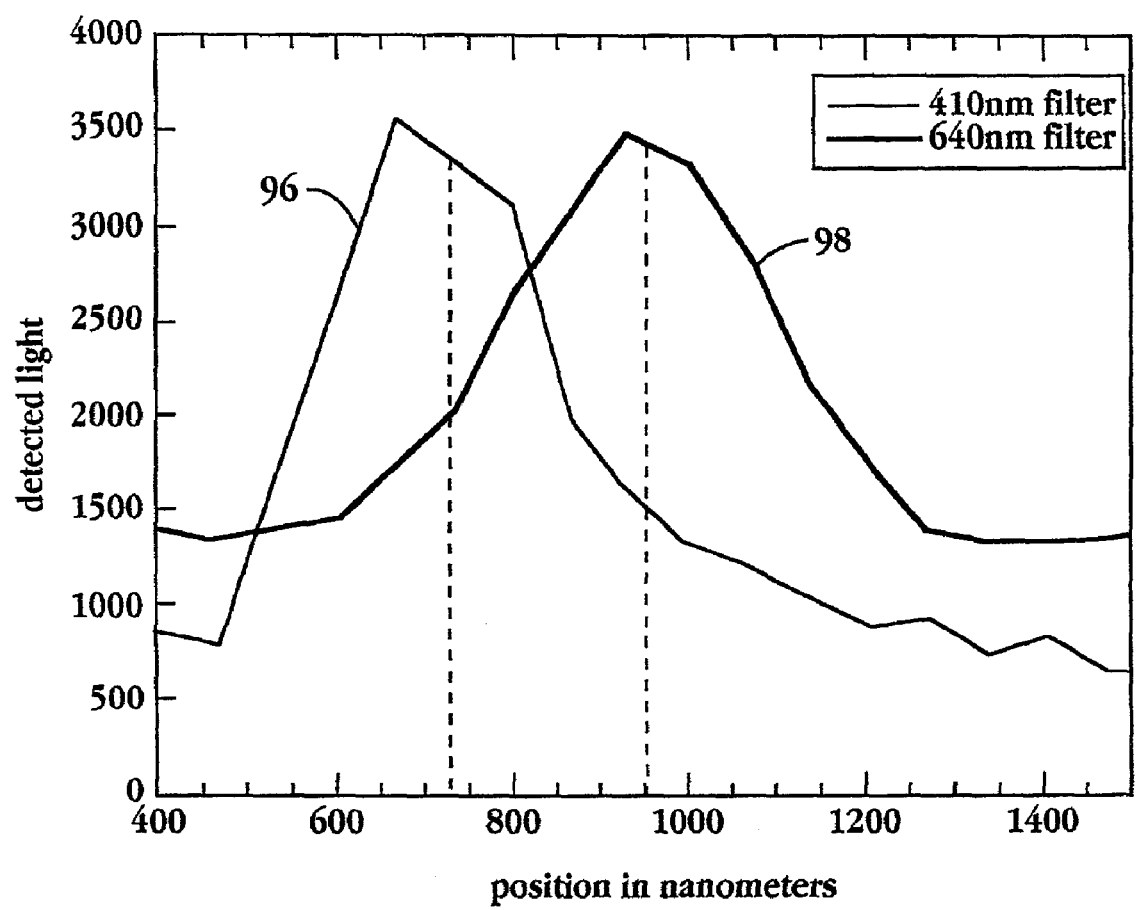
FIG. 8 is a graph of light intensity as a function of position in the image plane at two different bandwidths emitted by the plasmon resonant particles shown in FIG. 7.

Fluorescent in situ hybridization (FISH) may be performed with PREs (PRISH) instead of fluorescent labels. In this method, a PRE-labeled oligonucleotide is incubated with a DNA molecule of interest. If complementary sequences exist on the PRE bound oligonucleotides, the bound PREs may be observed. Alternatively, two PREs, each attached to a different oligonucleotide, are incubated with a DNA molecule of interest. If a genetic deletion associated with a particular disorder is present and the PREs bind on either side of the deleted region, they will be much closer together in the deletion versus the wild type. In this method, bound pairs of PREs may be detected by alterations in scattering parameters, or by observing correlated pairs of PREs of either the same or different spectral characteristics. PRISH allows detection of a smaller defect or selected genomic region due to gains in localization. With appropriately conjugated PREs, bound PREs may be observed at several locations along a strand of nucleic acid, providing information about several sites at one time. Distance measurements can also be made, as discussed in detail above. As illustrated by FIGS. 7 and 8, a 230 nm distance between PREs, which corresponds to approximately 640 base pairs, can be easily resolved to an accuracy of only tens of nanometers or less with optical microscopy. In addition, the use of PCR or other enhancement steps is unnecessary in contrast to FISH in which enhancement is usually required, although PCR enhancement can also be used in conjunction with PRE hybridization tests. Genetic deletions and mutations can also be detected using a ligase to join two adjacent strands of PRE coupled nucleic acid. If the PRE coupled strands hybridize in a precisely adjacent manner, denaturing will result in free strands of nucleic acid coupled to a pair of PREs. These bound pairs may then be observed as described above. If the strands hybridize at locations which are too close or too far apart, the ligase reaction will not occur, and bound pairs will not form. Bound pairs of PREs may also be produced with PCR methods if PREs are coupled to hybridizing strands of nucleic acid, and standard PCR techniques are used to amplify the quantity of target nucleic acid present.

In all of these procedures, the PREs can be conjugated to the oligonucleotides either before or after the oligonucleotides are bound to the target nucleic acid. Furthermore, such tests can be performed in vitro, or in a cell. Selective PRE hybridization is also advantageously applied to screening multiple nucleic acid containing sample wells comprising a library of different nucleic acid sequences. Such sample wells may be provided on library chip arrays or standard multiwell dishes.

PREs can also be coated with antibodies for use in assays analogous to enzyme-linked immunosorbent assay (ELISA) detection of various macromolecules. In one advantageous embodiment, multi-well dishes (i.e. 96-well microtiter plates) are coated with an antibody specific for a molecule of interest. A biological fluid to be tested is then placed in the wells containing the immobilized antibody. A PRE-labeled secondary antibody which binds a different region of the molecule than does the immobilized antibody is added to the wells. The plate is then read with a plate reader compatible with darkfield optical detection. The presence and level of PRE binding indicates the presence and amount of molecule in the biological fluid.

In another embodiment, a particular sample can also be visualized using multiple populations of PREs, each having a distinct spectral signature, and conjugated to separate antibodies which recognize different binding sites on a target molecule, or which recognize different target molecules. Alternatively, the PREs are coupled to a polyclonal antibody which recognizes a plurality of epitopes on the same target protein. The presence of two spectrally distinct PREs at the same location indicates a positive signal, while the separate presence of either particle would constitute an incomplete identification and would be rejected. This approach significantly reduces false positive signals in clinical diagnostic assays.

Additional advantages of PRE immunoassays include the fact that the ability to detect one PRE with a good signal to noise ratio obviates the need to amplify the signal by using secondary antibodies or enzymes and their substrates. This further eliminates non-specific background. Moreover, the ability to analyze the sample during processing by optical microscopy allows real time correction of incubation and wash conditions so as to further optimize signal to noise. PRE assays may be conveniently employed with essentially any target substance and various binding partners in direct, sandwich, and other widely used test formats, some of which are described in more detail below. Substances tested for and conjugated to PREs include proteins, nucleic acid, ligands, receptors, antigens, sugars, lectins, enzymes, etc.

EXAMPLE 7

PRP Assay of Goat-Antibiotin

Figure 9:
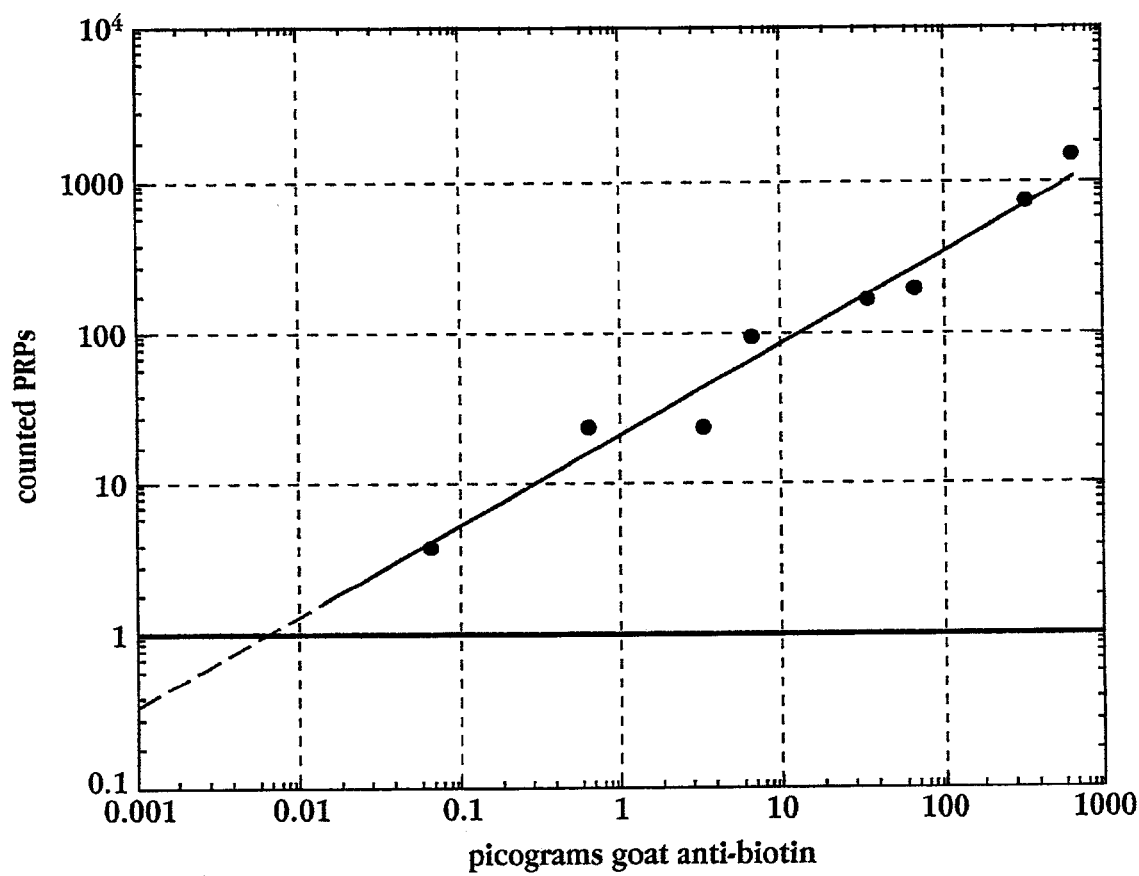
FIG. 9 is a graph showing the results of an assay performed with plasmon resonant labels.

The wells of a polystyrene multi-well dish were coated with biotinylated BSA. Regular BSA was added to block any remaining non-specific binding sites in the wells. Samples of goat-antibiotin antibodies ranging in concentration from 0.06 to 600 picograms (pg) were added to individual wells. A control sample having no goat-antibiotin antibodies was also assayed. PRPs bound to rabbit-antigoat antibodies were then added to each well and incubated. Unbound PRPs were washed from the wells, and bound PRPs in each well were observed with a darkfield optical microscope. Light sources in the field of view were analyzed according to the discrimination techniques described above, and the remaining scattering sites were individually counted in each well. The results of this test are shown in FIG. 9. The control sample had one count remaining after image processing, and is illustrated as the dark bar in FIG. 9. The number of counted PREs over the concentration range tested varied from 4 at 0.06 pg analyte, to over 1000 at 600 pg analyte.

Because it is advantageous to perform these assays with one or more populations of PREs having approximately uniform spectral characteristics, it is advantageous to form the PRE labels first under conditions which are conducive to forming such approximately uniform populations. As mentioned above, the binding of nucleation centers to binding sites, followed by metal enhancement and optical observation has been described, but this technique provides very little control over the spectral characteristics of the particles thus created. And even when these techniques have been performed, no effort to use the PRE scattering characteristics to discriminate background and make a highly sensitive assay has been made or proposed. Accordingly, PRE assays performed by first labeling target species with nucleation centers, and then metal enhancing them to form PREs, (rather than forming the PREs prior to binding) are still improved when light discrimination between PRE scatterers and background is performed. Furthermore, assays which use preformed optically observable sub-wavelength light emitters of any kind have not taken advantage of the technique of individually counting particles to create a sensitive assay. When spectral and spatial discrimination of background is performed, such counting can be useful for fluorescent or luminescent bead labels in addition to PRE labels. As will be discussed below, fluorescence can be enhanced by local plasmon resonance, and thus PRE enhanced fluorescent beads provide an additional sub-wavelength light emitting label useful for such assays.

It can also be appreciated that many variations of these types of assays may be performed with PRE labels. All of the various types of immunosorbent assays which are currently performed using fluorescent molecule labels may be performed with PREs instead. Sandwich and competition assays, for example, may be performed with PREs. In the first case, an entity such as an antibody having affinity for a target substance to be detected may be immobilized on the bottom of an assay well. A test sample including the target substance is added to the well, and the target substance binds to the first entity. A second entity, having affinity for a different portion of the target substance, may then be added to the well, wherein it binds to the target species. Finally, PREs bound to a third entity having affinity for the second entity are added to the well, which bind in turn to the second entity. After rinsing, it can be appreciated that PREs will only be bound to sites where the target substance has been previously bound. This test is very useful when the first and second entities mentioned above are antibodies having affinity to different epitopes on an antigen being assayed. The third entity, bound to the PREs, may then be an anti-species antibody, rather than being a specific binding partner of the target substance.

In a competition assay, a first entity may be immobilized in an assay well, and both PRE coupled second entities and target substances are added to the well, wherein the second entity and the target substance compete for binding to the first entity. When unbound PREs are separated, the number of PREs remaining in the well indicates the extent to which the target substance was able to occupy binding sites. In this type of assay, the PRE bound second entity may be the same as the target substance, or may be a different substance which also has an affinity for the first entity.

Those of skill in the art will recognize that PRE labels may be used to bind to a wide variety of molecular complexes in a wide variety of ways to produce a sensitive assay. As additional examples, the conjugate on the PRE label may be a specific binding partner of the analyte being tested for. It may be a specific binding partner of an immobilized analyte/antibody complex. As another alternative, PRE may bind to an immobilized antibody, but only if that immobilized antibody has previously bound an analyte molecule. Each of these various techniques may be especially suitable in a given assay, depending on the chemical nature of the analyte being tested for.

Furthermore, it will be appreciated that assays for multiple analytes can be performed simultaneously using populations of PREs having different spectral signatures. Populations of PREs different color or different polarization responses can be conjugated so as to recognize different target substances. When introduced into a matrix containing unknown concentrations of several different analytes, all of the assays set forth herein could be performed on several target substances at once by separately counting the PREs associated with each distinctive spectral characteristic.

PRE probes can also be used to screen in vitro combinatorial libraries. In some conventional versions of this technique, a drug receptor is labeled with a fluorophore then mixed with beads, the collection of which constitutes the combinatorial library, and spread out on a slide. The presence of a fluorescent bead indicates receptor binding and the presence of a potential drug bound to the bead. In one embodiment of the invention, the fluorescent receptor is replaced with a PRE-labeled receptor which increases the sensitivity and photostability of the assay, thereby allowing for the possible production of the original combinatorial library on smaller beads and the ability to synthesize and screen larger chemical libraries.

The libraries may also be synthesized on microchips, where the presence of a PRE probe indicates receptor binding. Recent applications of combinatorial libraries for improved drug discovery may thus be enhanced by using PRE probes as a method of detection of potential candidates. Selectively attached PRE increase the resolution and sensitivity of bio-chip detection schemes.

In all of these assays, PRE calibration is conveniently performed using PREs of different spectral characteristics than are used to detect the target entities. In essence, the assays are calibrated by introducing a predetermined quantity of PREs having a selected spectral characteristic to create a control population of PREs which can be detected and measured in conjunction with the PREs used for the assay function. As one specific sandwich assay calibration example, red PREs may be conjugated to the target entity being tested for, and a known amount (but of course much lower than a saturating amount) of this PRE conjugated target entity is added to the well along with the sample, either sequentially or simultaneously. After rinsing away unbound conjugated red PREs, antibodies to the target entity are added. After rinsing unbound target entity antibodies, blue PREs (for example) which are conjugated to an anti-species antibody are added which bind to the antibody to the target entity. After rinsing, both red and blue PREs are counted, and the red PRE count provides a calibration count. In an alternative to this sandwich format, a direct binding assay calibration may also be utilized, wherein different immobilized antibodies are provided on the bottom of the sample well, and the calibration PREs are conjugated to a specific binding partner to one of the immobilized antibodies.

Assays with PREs can also be performed in cells. Conjugated PREs can be bound to both fixed or free sites in cells and their locations individually observed. Well known techniques exist for placement of particles into cells, including high pressure bursts which cause the particles to perforate the cell membrane and electro-perforation in which high voltage discharges are used for the acceleration process (the PRE is typically charged prior to the electro-perforation techniques). Apparatus for performing these techniques are available from BioRad Laboratories of Hercules, Calif. PREs and PRE conjugates may also be introduced into cells by conventional transfection techniques including electroporation. PREs can also be placed into cells directly by piercing a cell membrane with a micropipette, and directly injecting one or more PREs into the cell. In a preferred embodiment, the PRE is coated (i.e. latex) by well known methods to protect it from biochemical damage.

In some advantageous embodiments of PRE assays within living cells, two populations of differently conjugated PREs are inserted into one or more cells. The separate conjugates associated with each separate population may be selected to bind to a different epitope on a target substance being manufactured in the cell. After injection into the cell, presence of the target substance will be indicated by PRE pairing, which is detected using the techniques described above. Depending on the nature of the target substance, it may be desirable to have PREs with similar, or disparate spectral characteristics associated with each conjugate.

It is advantageous to prepare wells for use with PRE assays which are suitable for observation with darkfield microscopy. For the multi-well plates to include a substrate suitable for darkfield microscopy, the well bottoms are advantageously manufactured with particular emphasis on uniformity, smoothness, and cleanliness so as to hinder the formation of light scattering imperfections. Such care is currently not taken in the production of standard 96 well dishes. In addition, the outside surface under the wells should also be relatively clean and smooth, as the outside surface also provides a light scattering surface which can introduce undesired background signals. In some advantageous embodiments, the surfaces of the wells have less than approximately 100, or even less than approximately 10, light scattering imperfections therein. As an additional method of increasing signal to noise ratios in these assays, the location of imperfections in a well can be documented, and a scattering signal from those locations can be ignored when the assay is performed with that particular well.

Typically, the field of view of the optical microscopes used in these assays comprises all of or portions of the bottom of the well. Thus, when low levels of analyte are being detected, it can be important to ensure that a minimum amount of analyte stick to the walls of the well, rather than to the bottom. It is accordingly advantageous to include a blocking agent on the walls of the well during production. To make such a well, a dish may be inverted and placed on a solution including a blocking agent such as BSA. If the dish is pushed down into the solution, or some of the air trapped in the wells is removed by sucking it out with a pipette or capillary, the BSA solution can be made to contact the walls of the well without touching the bottom of the well. After this step, the desired antibody or other binding agent is immobilized on the bottom of the well, and then additional blocking agent may be added to block remaining nonspecific binding sites on the well bottom.

Assay methods according to the invention can also be automated, employing, for example, the method and apparatus of the invention described in Section III. Automated plate readers are currently used for conventional assay techniques, and the principles for a robotic PRE plate reader are in some ways similar. As with currently available plate readers, a robotic sample loader may or may not be provided. A robotic PRE assay plate reader would advantageously include sample wells and a microscope for observing all or portions of the bottom of the wells. In some embodiments, a very small objective lens, which may be approximately 2 mm in diameter, is lowered down into the well and close to the well bottom to obtain a high numerical aperture while imaging a portion of the well bottom. In these embodiments, the PREs may be illuminated from the bottom with total internal reflection off the bottom of a transparent well bottom. As the light is gathered by the objective, light emitting entities can be detected and discriminated from background using automated image analysis techniques as described above. Counting the remaining discriminated particle sources can also be automatically performed. In some embodiments, the field of view of the microscope may be a portion of the assay well bottom, and the reader may be configured to discriminate and count particles in several regions of the same assay well until a certain predetermined count is read. Only after this count is reached will the reader move to a different assay well. This technique will save time by moving quickly from well to well when a large signal is present, and will take the time required to obtain adequate count statistics when low numbers of bound PREs are present in the well. The reader may also be configured to perform additional levels of discrimination depending on the count received. For example, a first discrimination based on the spatial deviation from the expected point spread function may be performed for all fields of view, but an additional spectral deviation measurement will be made when a low count value is obtained. All of the thresholds for performing various levels of discrimination can be preprogrammed into the reader, again insuring that wells having low PRE counts are analyzed to maximize signal to noise ratios, while time is saved on wells having a large number of counts, where signal levels are already high.

It will also be appreciated that mercantile kits including ingredients for performing assays described herein may be created having novel combinations of ingredients. Advantageously, such kits may include a container of PREs having approximately equal spectral characteristics. The PREs may be conjugated to selected biological molecules such as antibodies or other types of specific binding partners for selected substances. They may be coupled to reactive groups for custom formation of conjugate at a later time. Washing and blocking solutions may also be provided. A second container of PREs may also be provided for calibration or multiple assays as described above.

B. Binding of Two PRPs to Closely Spaced Target Sites

As discussed above, the spectral characteristics of light emitted by PREs is dependent on their proximity to other PREs. Changes in observed peaks in emitted frequencies, e.g., peak wavelength, spectral width at half intensity, the appearance of more than one peak, and changes in response to polarized light, etc., can all be observed as PREs approach and move away from one another. These features can even be used to determine the approximate distance between PREs, by measuring the extent of their interaction.

Agglutination and aggregation-dependent immunoassays are thus performed using PRE probes, and have the capability of single molecule detection. In one embodiment, two antibodies are each attached to a PRE probe having either the same or distinct spectral signatures. These antibodies bind to the same biomolecule of interest, but at non-competitive sites. The distance between the two binding sites will place the PRE probes in close proximity which are directly detected via narrow band illumination if the two PRE have separated plasmon resonance frequencies or if they have the same plasmon resonance frequency, by a unique spectral signature as a result of their interaction. For example, blood serum is added to a tube containing PRE probes which have been coated with antibodies specific for a particular serum component. After incubation, the sample is spread on a glass slide and the frequency of aggregated (i.e. close proximity) PRE probes is determined. This is compared to control slides on which the serum would either contain or not contain the molecule of interest. This technique has application to the multi-PRE labeling and consequent detection of peptides, nucleic acid oligomers or genes, as well as portions of or whole cells or viruses.

The measurement of binding constants between two entities is currently performed by several procedures. Macroscopic binding can be measured directly by, for example, isothermal titration calorimetry. Less direct methods include absorbance, fluorescence or changes in circular dichroism associated with complex formation. One problem associated with these methods is that a high concentration of material is required to observe a detectable change in signal, and at these high concentrations the sample may be essentially 100% complexed, thus preventing the measurement of a binding constant under these conditions. In a preferred embodiment, the two entities are labeled with PRE probes, equilibrium is reached, and the ratio of free to bound allows calculation of a binding constant.

The ability to detect when two PREs are adjacent is also important for assays of molecular association and dissociation. If two PREs are associated with suitable conjugate pairs and are mixed together, they will bind to form a pair or, if not restricted, higher complexes. As one example, PREs conjugated to oligonucleotides will form such pairs or complexes if the oligonucleotide sequences on different populations of PREs contain complementary sequences, or if the PRE bound oligonucleotide sequences are complementary to separate regions of a target oligonucleotide also present in the matrix.

C. Cleavage of a Linkage Between Two PREs

In this embodiment, a PRE is linked to another PRE thorough a cleavable linker, e.g., a peptide, oligonucleotide, oligosaccharide or other chemically or enzymatically cleavable linker. The aim of the linked composition is to detect single chemical or enzyme cleavage events, on the basis of an observable spectral change resulting from linked PREs becoming individual, unlinked PREs, in accordance with the Part B embodiment.

More generally, linked pairs of PRPs, are distinguished and, if the binding is disrupted, by, for example, enzymatic degradation of a peptide linker between the PREs or denaturation, this is reflected by the changes in the paired or complex PRE spectra. Operation of an enzyme may be monitored by this technique by observing an increased rate of complex formation or disassociation in the presence of the enzyme. One advantageous application of these methods includes monitoring the operation of a signal transduction cascade in a cell. Conjugated PREs are selected such that the presence of a product of a signal transduction cascade either disassociates previously bound PREs or binds disassociated PREs. The initiation of the cascade can thus be observed with optical microscopy in a living cell by observing association or disassociation of PREs in the cell.

Each PRE can be coated in such a way to result in a high probability of bound pairs by coupling with a linker such as a peptide or DNA molecule. As discussed herein, when two PREs with the same PR peak frequency are very close to each other, frequency shifts, additional resonances and polarization effects occur. If one wishes to determine whether a specific enzyme is present in solution, a linker is used which is susceptible to degradation by that enzyme. For example, serine proteases can be assayed by using a peptide linker containing a protease recognition site therein. After proteolysis, the spectra of the bound PREs changes dramatically as the PREs separate. In some cases, the PREs may be spatially separated far enough apart when linked such that they do not interact appreciably and retain essentially independent scattering spectra both when linked and unlinked. In this case, pair formation and disassociation can still be observed and measured by evaluating PRE positions with a CCD detector, and observe pairs of PREs having relative motion which indicates that they are linked.

VI. Additional Compositions and Applications of PREs

A. Monitoring Local Dielectric Environment

When a PRE in air is surrounded with a medium having a dielectric constant different from that of air, scattering parameters may change relative to the scattering parameters characteristic of the particle in air. This effect is reversible if the dielectric medium is removed. Such parameters include, for example, a change in intensity or shift in wavelength of the resonant peak, changes in the PREs response to polarized light, and a change in the number of resonant peaks. Shifts in the resonant peak and intensity are observed following the addition of liquids of different indices of refraction surrounding the PRE, and after they are removed by suitable washing steps, the PREs exhibit their prior characteristics. For many materials which exhibit plasmon resonance, raising the index of refraction of the surrounding medium will red shift the resonant peak to a longer wavelength.

The presence of specific substances of interest or other perturbations in a sample being tested may therefore be detected by noting the spectral response of PREs to substances which interact with the PRES. For example, a suitable sample can be prepared having PRE bound to a substrate. Selected molecules may be bound to the PRE surface. The optical scattering parameters (intensity, polarization dependence, angular dependence, wavelength dependence, etc.) of each such PRE are recorded. The sample is then treated with material which includes molecules of interest that selectively bind to the surface of the PRE in such a manner that after initial treatment and/or subsequent further treatments, the PRE scattering parameters have changed, confirming the local absorption of additional material or desorption of the additional or initial material, or other changes in the local dielectric environment. It can be appreciated that the initial PRE sample may be prepared as a test "library" or used to screen an "applied" library of proteins, antibodies, etc. These peak (D) Shift in Fluorescence Spectrum shifts and intensity changes can also be used to detect molecular perturbations such as association and dissociation due to changes in the PRE local dielectric environment.

Information concerning the properties of a subject matrix can also be obtained by observing the spectral dependence on the relative positions of a PRE and a nearby substrate such as a smooth Si surface. For example, having made a record of a PRE location and spectral signature in a given sample, one could add an enzyme or photolyze a bond, resulting in movement of the PRE from the substrate, thereby changing the PRE spatial and/or spectral signature. Indeed, if a pair of such PRE were bound together, and one moved while the other remained bound to the surface, the resulting spectral signatures would clearly indicate this event. Coatings on substrates can also be used to provide further flexibility in creating detection and analysis systems utilizing PREs. For example, a coating can be applied to a substrate which will bind a desired polypeptide or polynucleotide or a blocking coating can be applied which will block non-specific binding of the PRE conjugates. One suitable coating comprises, for example, one or more layers of dielectric materials which produce anti-reflection properties. The coating may also comprise one or more layers of dielectric material which will produce an enhanced radiation by the PRE of the light that enters the observing optical system. The coating can also be selected so as to displace the PRE a distance away from the basic substrate surface. A given polarization of the light scattered by the PRE will be inhibited or enhanced depending on the distance from a reflecting surface. For example, if a suitable spacer layer of $SiO_2$ is placed on the silicon, a nice point source image peaked in the center is observed as expected. If the $SiO_2$ layer is adjusted or another dielectric substance is used, conditions can be found related to the PRE resonant wavelength and the dielectric thickness and material where there is destructive and constructive interference of the PRE due to superposition of the light reflected from the substrate (interface) and the top of the dielectric layer. By using silicon or conducting surfaces, a noticeably different spectral signature is obtained than if the PRE moves away from contact with that surface or if a dielectric layer intervenes.

B. Monitoring Motion

Three dimensional PRE motion may be directly visualized using two observational lenses at right angles to each other, each yielding a two axis motion in the plane perpendicular to their respective optical axis. This is particularly suited to motions that are small compared to the depth of field of the objective lens. If the motion to be observed has a component which is large compared to the depth of focus of the objective lens, only one lens is used for three dimensional motion, whereby the "depth" direction is determined via a feedback signal that keeps the PRE intensity in focus on the image plane. The other two dimensions are determined in the usual manner. PRE distance from the substrate surface can also be monitored in TIR illumination systems by measuring the intensity of the light scattered by the PRE as it changes position. As the excitation electric field drops off exponentially with distance from the reflecting interface, PRE intensity will decrease as it moves away from the substrate surface.

Because PRE probes are so bright and so small they can be used for real-time determination of velocity and relative motion. For example, PREs may be used to monitor dynamic cellular processes including motor proteins (i.e. kinesin), cell division, vesicle transport, etc. PRE probes are particularly useful for in vivo temporal experiments over a broad range of timescales because they do not photobleach. PREs or precursor gold nucleating centers are attached to lipids which become incorporated into cell membranes. Specific PRE conjugates are designed to bind to their pair on cell surface receptors associated with the cell membrane. This method allows monitoring of, for example, ion channel openings. PREs may also be used to monitor movement of actin and myosin within muscle cells. PREs bound to or coated with conjugates can be introduced into cells. The conjugate will then bind to its binding partner within the cytosol, nucleus or on various organelle membranes. Activation of cell receptors, for example, by a particular drug, can lead to morphological changes in cell structure. PREs within or on cells can thus be used as an optical assay system for drug discovery or receptor activation. Once bound, the PRE can be localized and its motion observed. PREs may also be used to assay macroscopic motion. For example, a blood cell may be labeled and observed in circulation. Alternatively, the flow of blood or other liquid may induce a corresponding motion of the PRE. PREs can also be introduced into cells by a Biolistic device (BioRad Inc, Richmond, Calif.) or by electroporation.

By labeling any entity of interest with a PRE, the motion of that entity may be monitored using the detection process described herein by incorporating a suitable real time data acquisition and analysis system. Such a system may determine motion in a three dimensional sense and, if the movement is confined to a plane, in a two dimensional sense. Not only is precise information available about the motion in a specific system of interest, but also observable are changes in molecular motion after drug treatment or other changes in the physical and chemical environment such as alterations in temperature, pH, illumination, electric or magnetic field strength, or a change in concentration of any compound of interest.

PREs can also be used to monitor physical motion of more macroscopic objects. For example, a single PRE placed on an insect feeler could be used to sense its motion which could be regular or in response to an external molecule. This is particularly useful in detecting molecular responses to smell and pheromones. PREs are also ideal tools for allowing analysis of mechanical motion on a microscopic or sub-microscopic scale. By binding PREs to the components of so called "nano-bearings" or other micron sized machine parts, three dimensional motion can be visualized and analyzed on nanometer scales. In addition to the added expense of electron microscopes, motion is difficult to capture via electron microscopy as the electron microscope is a scanning device, and the field of view is therefore generated over time with sequential scans, rather than viewed in real time as is possible with optical microscopy. Furthermore, with electron microscopy, extensive sample preparation is required, in addition to an evacuated measurement area. These factors severely limit the potential application of electron microscopy to real time motion analysis.

C. Near-Field Effects

The applications of PREs discussed above have focused on the far-field observation of light scattered by the PREs. However, because PREs also generate intense, non-radiative short-range electric fields, they may be used to affect the physical, chemical, and spectroscopic properties of adjacent molecules in useful ways. The spectroscopic technique of Surface Enhanced Raman Scattering may be extended to include the specific enhancement of only those materials in the immediate vicinity of the enhancing PRE. For example, PREs may be conjugated to bind to a target having a known Raman signature. Successful binding can be detected by observing the surface enhanced Raman spectra of the target. They can also be useful for locally enhanced excitation and modified emission of nearby fluorophores. Surprisingly, PREs can produce enhanced emission from even high quantum efficiency fluorophores if the surface of the PRE is placed from approximately 1 to 5 nm away from the fluorophore. In contrast, it is generally thought that the presence of a metal quenches fluorophore emission of high quantum efficiency fluorophores. This fact can be used to create fluorescent labels having a much higher brightness or a changed lifetime, compared to when not so associated. A label which includes a plasmon resonant conductive core (such as a silver particle of 40-100 nm diameter) and a non-conductive shell, made, for example, from latex, may be created, wherein the shell has fluorescent or Raman-active molecules embedded on or within it. Preferably, the peak of the plasmon resonance has a significant overlap with the efficient excitation band for the fluorophore or Raman active molecule. When the label is illuminated, the plasmon resonance excitation of the core will greatly enhance the observed fluorescence. In accordance with the above discussion, the thickness of the non-conductive shell is preferably less than or equal to approximately 5 nm in order to produce fluorescence enhancement. The plasmon resonant core, selected to resonate at a chosen wavelength, thus dramatically improves label performance over the fluorescent latex particles currently commercially available.

Ellipsoidal PRE responses can also be advantageously employed in conjunction with fluorescence spectroscopy. Because ellipsoidal particles simultaneously permit resonance excitation at two or three distinct frequencies, they are particularly effective for localized excitation of a selected fluorophore by one such plasmon resonance, and then simultaneously effective for effecting the radiation (i.e. emission) of the excited fluorophore at wavelengths corresponding to the other plasmon resonance.

Thus, targeted PREs can induce very localized spectroscopic effects, again improving the collection of information about submicroscopic systems. Similar to the case of fluorescent resonance energy transfer (FRET), clustering of PREs gives rise to new optical properties including localized and Photonic Band Gap modes, which can be used to advantage in making highly responsive PRE-based detectors of molecular binding events.

D. Metrology and Instrumentation

Excited PREs can produce localized heating, and an individual PRE can be used to write to a polycarbonate substrate. As individual, highly localized light sources, PREs can be useful in precision lithography, photochemistry, or for inducing light activated chemical reactions.

PREs can also be used as markers in conjunction with all other non-optical forms of very high resolution microscopy, including electron, atomic force, and scanning tunneling microscopy. In these applications, a macromolecule of interest, such as a segment of DNA, is marked with one or more optically observable PREs. Preferably, the high resolution microscope is also equipped with darkfield optical microscopy apparatus for optically observing the portions of the surface to be imaged with the non-optical microscope. The PRE's bound to the molecule can be optically observed, and the relevant portion of the high resolution microscope, such as the atomic force or scanning tunneling probe tip, can be immediately positioned at a location of interest on the molecule to be observed. This can increase the efficiency of the use of high resolution microscopes, saving excess scanning time normally used to locate the object to be imaged. Atomic force, scanning tunneling, or any other type of scanning high resolution microscope can advantageously be constructed to incorporate darkfield microscopy systems in order to utilize this feature of PREs.

Industrial applications requiring high precision alignment or registration may also benefit from the use of PREs. One such application is the semiconductor manufacturing process, where lithographic masks must be precisely aligned with the semiconductor wafer being processed. Because PREs can be localized to a precision of a few nanometers or even less, a comparison of the position of one or more PREs on the semiconductor wafer with the position of one or more PREs on the lithographic mask can determine the location of the mask relative to the wafer at the nanometer level. As only relative positioning is important, either random or controlled PRE patterns on the mask and the wafer may be used.

Another application of the present invention takes advantage of the fact that PREs are essentially point sources of optical frequency light, having a diameter much less than the emission wavelength. Thus, they produce only the point-spread-function pattern characteristic of the instrument through which they are viewed, and not an image of their structure. This point spread function can be analyzed to detect imperfections in the optical system used to create it. As one example, an angular variation in the intensity of the circular fringes indicates a lens in the viewing system which has a circumferential asymmetry. Localizing the center of the Airy pattern at two or more emission wavelengths also evaluates a lens systems for chromatic aberrations.

The point source nature of PREs can also be used to test an optical system for its resolution. Using techniques described above for the placement of individual PREs at specific locations, a calibration set of PRE pairs can be created with varying distance between the PREs. It can then be determined how close two PREs must be before the central peaks of their respective point spread functions overlap to produce a single non-differentiated peak. To some extent, the same measurement can be performed by measuring the width of the peak of a single PRE in the focal plane with the lens system of interest.

Figure 10A:
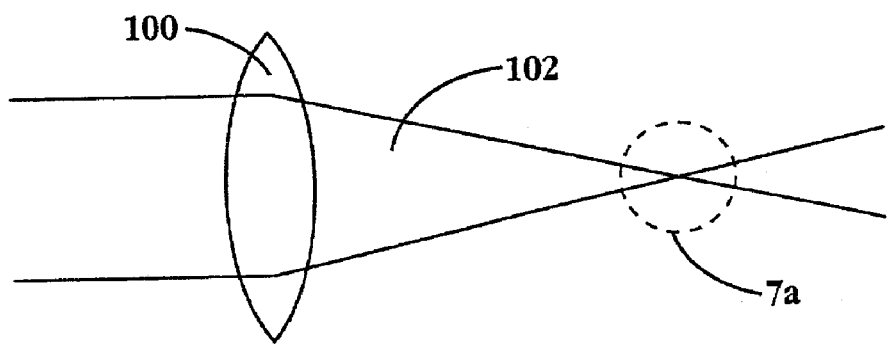
FIG. 10A illustrates a focused light beam having intensity profile characteristics measurable with plasmon resonant entities FIG. 10B illustrated the placement of a plasmon resonant entity within the focused light beam of FIG. 10A.
Figure 10B:
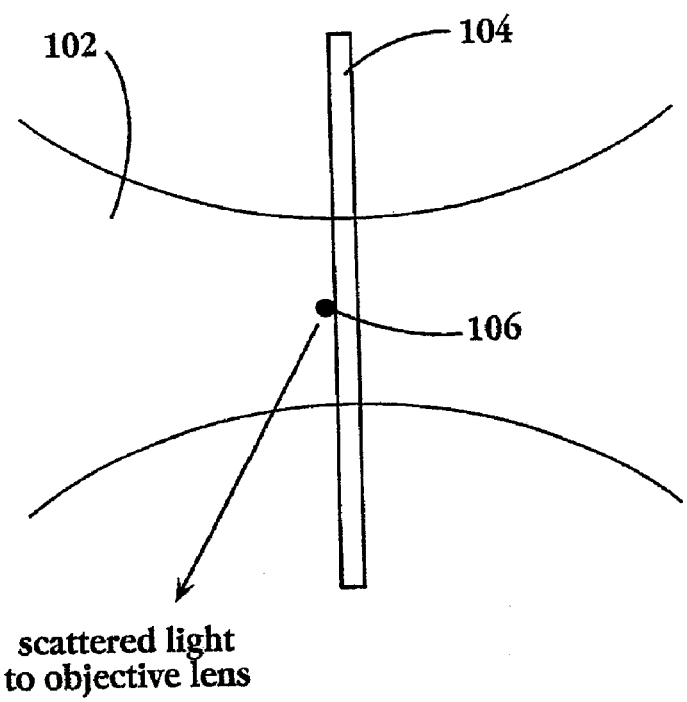

PREs may also be used to profile the intensity distribution of focused light beams, thereby gathering information concerning the properties of lenses and other optical systems used to produce such beams. As illustrated in FIGS. 10A and B, a focusing lens 100 produces a light beam 102 focused to a narrow beam in the lens focal plane. As is well known in the art, the beam is not focused to a point at the focal plane, but the intensity has an approximately Gaussian intensity as a function of distance away from the center of the focused beam. The details of the intensity as a function of position in the focal plane will depend on the characteristics of the optical system which produced the focused beam.

Referring now to FIG. 10A, a thin transparent plate 104 may be placed in the beam 102 at the focal plane. The transparent plate 104 includes a PRE mounted thereon. Preferably, of course, the peak of the plasmon resonance response of the PRE is selected to approximately match the predominant frequency band of the incident light beam 102. It can be appreciated that the intensity of the light scattered by the PRE will depend on the intensity of the illumination. Accordingly, if the plate 104 or beam 102 is moved such that the PRE moves to different locations in the focal plane, the intensity as a function of position can be determined by collecting scattered light with a suitably placed objective lens of an observing microscope. As with other darkfield techniques described above, the objective of the observing microscope may be placed so that it collects light emitted by the PRE but does not collect light transmitted through or specularly reflected by the plate 104. This system may be used to test the characteristics of solid-immersion-lenses, lasers, and other optical systems.

E. Object Identification

Still another application of the present invention is the labeling and identification of paper or plastic items subject to forgery such as paper currency or credit cards, or identification badges. Either random or pre-defined patterns of PREs may be bonded to the surface of the item. In advantageous embodiments, the PREs are coated with a protective layer or film. Later observation of the proper PRE pattern on the item with microscopy techniques as described above can be used for authentication purposes. Such authentication can be implemented via a pattern recognition system on a computer, allowing for real time authentication at point-of-sale terminals, facility entry locations, and the like. Alternatively, a magnetic strip, bar code, or other data storage media may be placed on the item (e.g., a credit card) in addition to the PRE arrangement. A coded version of the PRE array is also stored in this media, and a match indicates that the item was validly created. Of course, a cryptographic algorithm which produces a matching magnetic code based on the PRE array that cannot feasibly be deduced from the array itself should be used, and such algorithms are well known in the cryptographic art.

G. Forensics

The robustness and easy visibility of PREs also makes them ideal for several forensic applications. Bodily oils, fluids, DNA, etc. which is present in fingerprints can bind PREs, making the fingerprint easily visible under appropriate illumination. Many different goods may also be labeled with PREs to provide traceability. PREs having different scattering characteristics can be mixed with explosives, food, drugs, poisons or other toxins, etc. The particular PRE could provide source identification. PREs are ideal for this application because of their resistance to degradation and the ability to detect even single individual PREs in a sample.

H. Identifying Small Molecules in Combinatorial Libraries by Raman Spectrum PREs PREs can also be differentiated by the characteristics of molecules which are attached to their surface which may be provided in addition to the one or more conjugate molecules. Surface enhanced Raman scattering from Raman active molecules adjacent to individual PREs has been reported (Nie and Emory, Science, Volume 275, 1102-1106, 1997). If molecules with different Raman spectra are attached to different populations of PREs, PREs from different populations may be identified by their different Raman scattering signatures. Given the wide variety of Raman molecules available, a large number of differentiable probes are possible which may be particularly useful in conjunction with combinatorial library techniques. The use of Raman markers may also be used as an alternative way (in addition to four different plasmon resonance wavelengths) to produce four differentiable PRE populations, which would be useful in DNA sequencing techniques which use four differentiable markers, one for each base. Fluorescent molecules may also be bound to PREs to provide an additional marker, as can oligonucleotides, which are distinguished by their preferential hybridization properties rather than spectrally. If desired, PREs having a conductive resonant core and a non-conductive dielectric shell such as latex may include embedded fluorescent molecules in the dielectric shell. This label embodiment is discussed in more detail below. It can be appreciated as well that combinations of different resonant scattering characteristics, different fluorescent markers, and different Raman markers can be utilized to prepare hundreds or even thousands of spectrally differentiable probes. For example, a library may include four different plasmon resonance signatures, four different fluorescent signatures, and ten different Raman signatures, thereby producing 160 different distinguishable probes by different combinations of the available spectral signatures. Accordingly, populations of PREs may be distinguished based on differences in size or shape, or by differences in material bound thereto.

Furthermore, known techniques of combinatorial chemistry can be used to simultaneously synthesize a marker molecule and a conjugate molecule onto PREs in a simultaneous series of molecular assembly steps. In some embodiments, this process would start with a label precursor entity which comprises a PRE having one or more reactive groups bonded to it which may form a base on which combinatorial chemical synthesis may initiate. The reactive groups may include, for example, a phosphates, aldehydes, carboxyls, alcohols, amides, sulfides, amino acids, or nucleic acid bases. For example, a selected Raman active molecule could be synthesized simultaneously with an oligonucleotide conjugate. Alternatively, a library of drug candidate compounds may be synthesized simultaneously with identifying oligonucleotide markers.

I. Cell Sorting

PRE probes are also suitable for cell sorting, analogous to fluorescent activated cell sorting (FACS). A mixed cell population is analyzed for one cell type expressing a particular surface antigen using a particular PRE probe. In addition, several cell types are isolated by simultaneously using multiple PRE probes because of the number of uniquely identifiable PRE probes with distinct spectral signatures that can be made. It is contemplated that all of the PRE detection and localization methods described herein can be fully automated to produce, among other items, cell sorters. With a PRE cell sorter, it is advantageous to pass the cell population of interest substantially one at a time into the field of view of a darkfield microscope. The detection, discrimination, and analysis techniques described in detail above can be used in the cell sorting context to identify PRE labelled cells.

Many different cell routing schemes may be used in such an apparatus. In one advantageous embodiment, the cells are deposited into a stream of fluid, such as water, which is constrained to move within the confines of a surrounding shell of a second fluid, such as an oil, which is substantially immiscible in the first fluid. This forces the cells to remain confined to a small region for darkfield viewing as they pass through the field of view of the microscope. Preferably, the indices of refraction of the two fluids are approximately equal, to minimize reflections of incident light at the interface between them.

In addition, PRE labeling can be used in addition to, rather than as a substitute for, fluorescent labeling in a cell sorting technique. In this case, fluorescent labels and PRE labels are made to bind to the same target cells. The cell sorting may be done based on an observation of the fluorescent marker. If a portion of the sorted cells are saved as an archival record of the result of the sorting process, the PRE can be used to verify successful sorting in the future. This is more effective than observing the fluorescence of stored samples, due to the stability and non-photobleaching properties of the PRE.

A further application of the same technology is performed in vivo or ex vivo. In this technique, cells are permeabilized and PRE probe(s) attached to antibodies against a cellular biomolecule of interest are introduced into the permeabilized cells. The cells are then incubated with a combinatorial chemical library. The viable cells are spread out on a slide and the cells are selected which have been "affected" by the chemical library. "Affected" could indicate a change in localization or distribution of PRE probes due to a change in localization of the attached biomolecule, or it could indicate a clustering of PRE probes leading to a new spectral signature. Because any entity of interest (i.e. cell, DNA, organelle) can be labeled with a PRE, it can then be optically detected because the collection of PRE can be observed moving as a unit.

J. Clinical Applications of PREs

PREs can also be used in a wide variety of clinical applications. One significant area is in the diagnosis of different conditions in animals, including humans, which can be identified by the selective binding of conjugate to specific organs in the animal. In this technique, PREs having selected scattering characteristics may be injected into the bloodstream or ingested by the animal. These PREs may further be bound to an antibody or other conjugate to target or identify the presence of a particular substance in the animal. Tissue may then be removed form the animal and tested for the presence of PREs under a microscope. If desired, control PREs which are not bound to the specific binding conjugate can also be injected or ingested to determine the non-specific binding background. These techniques have been developed with colored latex particles as the probe, and reagents for performing these tests with the latex particles are commercially available from, for example, Triton Technologies of San Diego, Calif. and Molecular Probes of Eugene, Oreg. The use of PREs, due to their brightness, biocompatibility, and resistance to degradation will improve the sensitivity of such tests.

Cell modification and therapy techniques such as gene therapy may also be enhanced with PREs. In this case, cells having the desired genetic characteristics are labeled with PREs and selected with a cell sorter using the techniques set forth above. Selected cells are then placed in a patient. If desired, the PRE can be disassociated and removed prior to placement in the patient.

Selective heating and drug delivery is also possible with PREs. If PREs are localized in a selected tissue or region of a patient, they can be illuminated so as to locally heat the tissue or region without significant affect on neighboring areas of the body. The administration and activation of light activated drugs is also enhanced with PREs. Light activated drugs can be activated with far less total light energy by being bound to a PRE where the electric field will be enhanced. The use of light activated drugs to treat breast cancer has received recent attention, and may be improved by binding the drugs to PREs to enhance their activation at locations deeper in the tissue.

The application of optical PRE detection and analysis to biochemical systems is considered to provide many advantages over current labeling techniques, and appears to comprise an area where PRE analysis can have a large impact. Other areas, however, may also benefit from the PRE detection and spectral analysis of the present invention.

From the foregoing, it will be appreciated how various objects and features of the invention have been met. The method and apparatus of the invention are ideally suited to a variety of target-interrogation tasks that have been difficult or impossible heretofore, including, as representative examples: [0318]1. detecting single molecule events; [0319]2. resolving sub-wavelength distance relationships in a biological target in a natural hydrated state; [0320]3. direct spatial mapping of selected target sites on a biological target, such as direct mapping of selected sequences in a chromosome for purposes of chromosome mapping; and [0321]4. optical reading of microencoded information;

The method and apparatus can further be applied to a wide variety of diagnostics applications, to achieve improved sensitivity, spatial and distance information, ease of sample preparation, and flexibility in the type of target sample that can be interrogated.

Although the present invention has been described with respect to particular methods, compositions, and devices. It will be appreciated that various changes and modifications can b made without departing from the invention.

The invention claimed is:

1. A composition of plasmon resonant particles (PRPs) having first and second populations of PRPs having first and second different surface bound molecules or entities for use in identifying a target having first and second ligand-binding sites, wherein the first and second surface bound molecules are first and second ligands effective to bind to said first and second ligand-binding sites, respectively.

2. The composition of claim 1, wherein at least 80% of the PRPs in the composition are in one or more of the populations and have a spectral emission wavelength in the 400-700 nm wavelength range.

3. The composition of claim 2, wherein the particles have a composition selected from the group consisting of (i) a solid silver particle, (ii) a silver particle with a gold core, and (iii) a particle with a dielectric core and an outer silver shell of at least about 5 nm.

4. The composition of claim 1, wherein the particles have a composition selected from the group consisting of (i) a solid silver particle, (ii) a silver particle with a gold core, and (iii) a particle with a dielectric core and an outer silver shell of at least about 5 nm.

5. The composition of claim 1, wherein the particles have localized at their surfaces, one from the following group: (i) surface-attached ligands adapted to bind to ligand-binding sites on a target, where the ligand/ligand-binding sites are conjugate binding pairs, (ii) fluorescent molecules, (iii) Raman-active molecular entities, and (iv) a blocking reagent to prevent non-specific binding, and (v) a coating with functional groups for covalent coupling to the PRPs.

6. The composition of claim 5, wherein the surface localized ligand is one of a conjugate pair selected from the group of pairs consisting of antigen/antibody, hormone/receptor, drug/receptor, effector/receptor, enzyme/substrate, lipid/lipid binding agent and complementary nucleic acids strands.

7. The composition of claim 1, wherein the first and second surface-localized molecules are oligonucleotides having sequences that are complementary to first and second proximate sequence regions of a target polynucleotide.

8. The composition of claim 1, wherein the first and second surface-localized entities are Raman-active molecular entities with different Raman spectral characteristics.

9. The composition of claim 1, having first and second populations of PRPs, each with a different shape, at least one of which is spherical or tetrahedral.

10. A composition of plasmon resonant particles (PRPs) useful for identifying a target having first and second ligand-binding sites, wherein: (a) the composition comprises a first and a second population of PRPs having different surface-attached ligands adapted to bind to ligand-binding sites on the target, wherein the ligand/ligand-binding sites are conjugate binding pairs and first and second surface bound molecules are first and second ligands effective to bind to the target's first and second ligand-binding sites, respectively; (b) the PRPs have a width at halfheight of less than 100 nm; (c) the emission spectrum of the PRPs in a single population is within 40 nm of a defined wavelength; (d) at least 80% of the PRPs in the composition satisfying criterion (b) are in one or more of the populations and have a spectral emission wavelength in a single range selected from the group consisting of: (i) >700 nm; (ii) 400-700 nm; and (iii) <400 nm; and (e) the first population of PRPs has at most a 30% overlap in the second population of PRPs.

11. The composition of claim 10, wherein the first and second surface bound molecules are oligonucleotides having sequences that are complementary to first and second proximate sequence regions of a target polynucleotide.

* * * * *